(12) United States Patent
Kotseroglou

(10) Patent No.: US 8,574,840 B2
(45) Date of Patent: Nov. 5, 2013

(54) ROTATION-DEPENDENT TRANSCRIPTIONAL SEQUENCING SYSTEMS AND METHODS OF USING

(75) Inventor: Theofilos Kotseroglou, Hillsborough, CA (US)

(73) Assignee: Eve Biomedical, Inc., Redwood City, CA (US)

( * ) Notice: Subject to any disclaimer, the term of this patent is extended or adjusted under 35 U.S.C. 154(b) by 0 days.

(21) Appl. No.: 13/403,645

(22) Filed: Feb. 23, 2012

(65) Prior Publication Data
US 2012/0214171 A1    Aug. 23, 2012

Related U.S. Application Data

(60) Provisional application No. 61/463,850, filed on Feb. 23, 2011, provisional application No. 61/574,270, filed on Jul. 30, 2011.

(51) Int. Cl.
*C12Q 1/68* (2006.01)
*C12P 19/34* (2006.01)
*C12M 1/34* (2006.01)

(52) U.S. Cl.
USPC ....... 435/6.1; 435/6.12; 435/91.2; 435/287.2; 435/288.7

(58) Field of Classification Search
None
See application file for complete search history.

(56) References Cited

U.S. PATENT DOCUMENTS

| | | | |
|---|---|---|---|
| 7,556,922 B2 | 7/2009 | Block et al. | |
| 2002/0067417 A1* | 6/2002 | Tan et al. | 348/308 |
| 2003/0194740 A1 | 10/2003 | Williams | |
| 2007/0077575 A1 | 4/2007 | McAllister et al. | |
| 2008/0020392 A1 | 1/2008 | Block et al. | |
| 2009/0208957 A1* | 8/2009 | Korlach et al. | 435/6 |
| 2010/0184020 A1 | 7/2010 | Beer | |

OTHER PUBLICATIONS

Pomerantz et al. Nano Letters (2005) 5(9): 1698-1703 + 3 pages of Supplementary Information.*
Han et al. CMOS Integrated DNA Microarray Based on GMR Sensors. Electron Devices Meeting, 2006, IEDM '06 International, 4 pages.*
Abbondanzieri et al., "Direct observation of base-pair stepping by RNA polymerase," *Nature*, 2005, 438:460-465.
Akeson et al., "Microsecond Time-Scale Discrimination Among Polycytidylic Acid, Polyadenylic Acid, and Polyuridylic Acid as Homopolymers or as Segments Within Single RNA Molecules," *Biophys. J.*, 1999, 77:3227-3233.
Braslavsky et al., "Sequence information can be obtained from single DNA molecules," *PNAS USA*, 2003, 100:3960-3964.
Davenport et al., "Single-molecule study of transcriptional pausing and arrest by *E. coli* RNA polymerase," *Science*, 2000, 287:2497-2500.
Gosse et al., "Magnetic Tweezers: Micromanipulation and Force Measurement at the Molecular Level," *Biophys. J.*, 2002, 82:3314-3329.
Greenleaf et al., "Passive All-Optical Force Clamp for High-Resolution LaserTrapping," *Phys. Rev. Lett.*, 2005, 95(20):208102, 8 pages.
Harada et al., "Direct observation of DNA rotation during transcription by *Escherichia coli* RNA polymerase," *Nature*, 2001, 409:113-115.
Herbert et al., "Sequence-Resolved Detection of Pausing by Single RNA Polymerase Molecules," *Cell*, 2006, 125:1083-1094.
Kasas et al., "*Escherichia coli* RNA Polymerase Activity Observed Using Atomic Force Microscopy," *Biochem.*, 1997, 36:461-468.
Lipfert et al., "A method to track rotational motion for use in single-molecule biophysics," *Rev. Sci. Instrum.*, 2011, 82:103707.
Pomerantz et al., "A Tightly Regulated Molecular Motor Based upon T7 RNA Polymerase," *Nano Letter*, 2005, 5:1698-1703.
Ribeck & Saleh, "Multiplexed single-molecule measurements with magnetic tweezers," *Rev. Sci. Instrum.*, 2008, 79:094301.
Sanger et al., "DNA sequencing with chain-terminating inhibitors," *PNAS USA*, 1977, 74:5463-5467.
Shaevitz et al., "Backtracking by single RNA polymerase molecules observed at near-base-pair resolution," *Nature*, 2003, 426:684-687.
Shundrovsky et al., "A Single-Molecule Technique to Study Sequence-Dependent Transcription Pausing," *Biophys. J.*, 2004, 87:3945-3953.
Thomen et al., "Unraveling the mechanism of RNA-polymerase forward motion by using mechanical force," *Phys. Rev. Lett.*, 2005, 94:128102.
Greenleaf et al., "High-resolution single-molecule optical trapping measurements of transcription with basepair accuracy: instrumentation and methods," *Proceedings of SPIE*, Jan. 1, 2007, 664406-664406-8.
Zlatanova et al., "Single-molecule approaches reveal the idiosyncrasies of RNA polymerases," *Structure*, Jun. 1, 2006, 14(6):953-966.
Deniz et al., "Single-molecule biophysics: at the interface of biology, physics and chemistry," *J R Soc Interface*, Jan. 6, 2008, 5(18):15-45.
Capitanio et al., "Exploring molecular motors and switches at the single-molecule level," *Microsc Res Tech.*, Nov. 2004, 65(4-5):194-204.
Rosenberg et al., "Rotational motions of macro-molecules by single-molecule fluorescence microscopy," *Acc Chem Res.*, Jul. 2005, 38(7):583-593.
Authorized Officer Leslie Ripaud, International Search Report and Written Opinion of the International Searching Authority, PCT/US2012/026339, mailed Jul. 4, 2012, 17 pages.

\* cited by examiner

*Primary Examiner* — Angela M Bertagna
(74) *Attorney, Agent, or Firm* — Fish & Richardson P.C.

(57) ABSTRACT

Provided herein are rotation-dependent transcriptional sequencing methods and systems.

60 Claims, 16 Drawing Sheets

SEQUENCE LISTING

<160> NUMBER OF SEQ ID NOS: 8

<210> SEQ ID NO 1
<211> LENGTH: 66
<212> TYPE: DNA

```
<213> ORGANISM: Artificial Sequence
<220> FEATURE:
<223> OTHER INFORMATION: synthetic oligonucleotide

<400> SEQUENCE: 1
gcagtaatac gactcactat agggagaggg agggatggag cctttaagga ggtcaaatgg    60
ctaacg                                                               66

<210> SEQ ID NO 2
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 2
ggcatctaga tgcatcccta tgcagtccta atgc                                34

<210> SEQ ID NO 3
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 3
ggcagctagc taaacatggc gctgtacgtt tcgc                                34

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
agcctttcgg atcgaacacg atga                                           24

<210> SEQ ID NO 5
<211> LENGTH: 16
<212> TYPE: RNA
<213> ORGANISM: Artificial Sequence
<220> FEATURE:
<223> OTHER INFORMATION: hypothetical transcription product

<400> SEQUENCE: 5
ugauguggga aagucg                                                    16

<210> SEQ ID NO 6
<211> LENGTH: 15
<212> TYPE: DNA
<213> ORGANISM: Artificial Sequence
<220> FEATURE:
<223> OTHER INFORMATION: DNA sequence of hypothetical transcription
      product of SEQ ID NO:5

<400> SEQUENCE: 6
actcacccct ttcag                                                     15

<210> SEQ ID NO 7
<211> LENGTH: 50
<212> TYPE: RNA
<213> ORGANISM: Artificial Sequence
<220> FEATURE:
<223> OTHER INFORMATION: hypothetical transcription product

<400> SEQUENCE: 7
```

```
gcgagcugau cugcgcagcg aacauggagc ugagccugga ucugcuggcu          50

<210> SEQ ID NO 8
<211> LENGTH: 32
<212> TYPE: RNA
<213> ORGANISM: Artificial Sequence
<220> FEATURE:
<223> OTHER INFORMATION: hypothetical transcription product

<400> SEQUENCE: 8
ucugcgcagc gagcauggag cugaaccugg au                             32
```

ROTATION-DEPENDENT TRANSCRIPTIONAL SEQUENCING SYSTEMS AND METHODS OF USING

CROSS REFERENCE TO RELATED APPLICATIONS

This application claims benefit under 35 U.S.C. 119(e) to U.S. Application No. 61/463,850, filed on Feb. 23, 2011, and U.S. Application No. 61/574,270, filed on Jul. 30, 2011.

TECHNICAL FIELD

This disclosure generally relates to nucleic acid sequencing systems and methods and compositions that can be used in such systems and methods.

BACKGROUND

Several techniques are currently available for detection and typing of bacterial and viral pathogens. This includes methods employing:
1) indirect determination of genetic sequence including species/strain-specific PCR, repetitive sequence-based PCR (rep-PCR), pulse-field gel electrophoresis (PFGE), and optical DNA mapping,
2) direct determination of the sequence by either multi-locus sequence typing (MLST) or whole bacterial genome sequencing, or
3) a combination of the above such as determination of the base composition of PCR products by mass spectrometry.

The first group of techniques (Cepheid, PathoGenetix, Inc., OpGen, Inc.) has lower resolution and discrimination power compared to the second group of techniques and is limited by the small number of conserved genomic regions interrogated. The techniques in the second group, however, have been prohibitively expensive and provide only low throughput, although, with the introduction of $2^{nd}$ (SOLiD and PGM by Life Technologies/Ion Torrent, Illumina, Roche 454, Complete Genomics) and $3^{rd}$ (Pacific Biosciences, Helicos) generation high throughput sequencing techniques, the per sample cost is trending below $10,000. Moreover, the currently available sequencing technologies suffer from either complex sample preparation and DNA cluster generation (SOLiD and IonTorrent by Life Technologies, Roche 454, Complete Genomics, Illumina), short read length (Helicos, SOLiD, Illumina), or high error rate (Pacific Biosciences). Additionally, the currently available single-molecule sequencing instruments (Pacific Biosciences and Helicos) are bulky, very expensive, and require highly trained personnel to operate. The third group of techniques (Ibis Biosciences Inc.) is able to determine the nucleotide composition of only relatively short sequences of PCR products and suffers from all limitations of conventional PCR.

In contrast to currently available single molecule technologies (Helicos, Pacific Biosciences), the rotation-dependent transcriptional sequencing described herein does not require development of mutant polymerases capable of incorporating modified nucleotides, expensive labeled nucleotides, or lasers and costly high-speed cameras. Thus, the rotation-dependent transcriptional sequencing described herein can be integrated into inexpensive portable point-of-care systems.

In addition, the rotation-dependent transcriptional sequencing described herein allows for ultimate flexibility and fast reconfiguration; permitting rapid response to unforeseen endemic threats, emerging diseases, pandemics and new bioterror threats by simply updating the platform-associated nucleic acid database and software without any change of the reagents. This is in contrast to numerous diagnostic platforms exploiting PCR, where significant time is required for assay reconfiguration and validation before platform redeployment to address any new targets. This is also in contrast to non-sequencing single-molecule Genome Sequence Scanning platform using Direct Linear Analysis (DLA) technology (PathoGenetiX), which relies upon a spatial pattern of tags separated by at least 3 kb and makes this technology insensitive to sub-kb insertions or deletions as well as single-nucleotide variances.

Furthermore, the rotation-dependent transcriptional sequencing described herein allows for ultimate multiplexing capability. While PCR- and microarray-based methods are limited by the detection of only known infectious agent(s) and cannot identify variants that are mutated or bioengineered (i.e. with a single nucleotide difference), the rotation-dependent transcriptional sequencing described herein is, in a sense, "target agnostic," as the methods decode primary structure of any and all DNA molecules in or extracted from the specimen, and, thus, is capable of detecting and identifying thousands of known or unknown (e.g., genetically-modified) targets simultaneously. Such an inherited "broadband" multiplexing capability provided by the systems and methods described herein is in contrast to approaches employing PCR that require specific sets of reagents (primers and probes) for detection of each pathogen. Additionally, PCR-based technologies are limited by the number of assays allowed in multiplexed reactions simply due to the nature of PCR, or by the need to split the sample (i.e., containing the target nucleic acids) between multiple reactions, thereby compromising the sensitivity of detection and the accuracy of quantification.

SUMMARY

Rotation-dependent transcriptional sequencing relies upon the RNA polymerase being immobilized relative to the solid surface. As a consequence of transcription, the RNA polymerase exerts torque on the nucleic acid, which, in turn, manifests itself as rotation of a tag attached to the nucleic acid.

In one aspect, a method of determining the sequence of a target nucleic acid molecule is provided. Such a method generally includes contacting an RNA polymerase with a target nucleic acid molecule under sequencing conditions, detecting the rotational pattern of the rotation tag, and repeating the contacting and detecting steps a plurality of times. Typically, sequencing conditions include the presence of at least one nucleoside triphosphate, and the RNA polymerase is immobilized on a solid substrate, where the target nucleic acid molecule comprises a rotation tag. The sequence of the target nucleic acid molecules is based, sequentially, on the presence or absence of a change in the rotational pattern in the presence of the at least one nucleoside triphosphate.

In some embodiments, the RNA polymerase is a bacteriophage RNA polymerase (e.g., a T7 RNA polymerase, a T3 RNA polymerase). In some embodiments, the RNA polymerase is a bacterial RNA polymerase (e.g., E. coli RNA polymerase). In some embodiments, the RNA polymerase is immobilized on the solid surface via a His-tag. Representative target nucleic acid molecules can be prokaryotic, bacterial, archaeal, and eukaryotic. Target nucleic acid molecules typically are double-stranded, and can be comprised within a biological sample. The target nucleic acid molecule further can include a RNA polymerase promoter sequence.

In some embodiments, the rotation tag includes a first tag and a second tag. For example, in some embodiments, the first tag is magnetic. A representative solid substrate is made from glass. Other representative solid substrates include a CMOS or CCD. In some embodiments, the sequencing conditions include the presence of a single nucleoside triphosphate; in some embodiments, the sequencing conditions include the presence of four nucleoside triphosphates, where a first nucleoside triphosphate of the four nucleoside triphosphates is present in a rate-limiting amount.

In some embodiments, the detecting step includes projecting light onto the rotation tag. In some embodiments, the detecting step further includes observing the rotational pattern via a microscope. In some embodiments, the detecting step further includes capturing the rotational pattern on a CMOS or CCD. In some embodiments, the detecting step includes capturing the rotational pattern as a magnetic image. In some embodiments, the magnetic image is captured on a GMR sensor or a MRAM array. In some embodiments, the detecting step includes capturing the rotational pattern as an electric field. In some embodiments, the image is captured on a RAM sensor.

Such methods also can include applying a directional force on the target nucleic acid molecules. For example, directional force can be produced using a magnet, or using flow or pressure.

In another aspect, a method of determining the sequence of a target nucleic acid molecule is provided. Such a method typically includes providing a solid substrate onto which RNA polymerase is immobilized; contacting the RNA polymerase with the target nucleic acid molecule under first sequencing conditions, wherein the target nucleic acid molecule comprises a rotation tag, wherein the first sequencing conditions comprise the presence of four nucleoside triphosphates, where a first nucleoside triphosphate of the four nucleoside triphosphates is present in a rate-limiting amount; detecting the rotational pattern of the rotation tag under the first sequencing conditions; and determining positional information of the first nucleoside triphosphate along the target nucleic acid molecule based on a change in the rotational pattern.

Such a method can further include providing a solid substrate onto which RNA polymerase is immobilized; contacting the RNA polymerase with the target nucleic acid molecule comprising the rotation tag under second sequencing conditions, wherein the second sequencing conditions comprise the presence of four nucleoside triphosphates, where a second nucleoside triphosphate of the four nucleoside triphosphates is present in a rate-limiting amount; detecting the rotational pattern of the rotation tag under the second sequencing conditions; and determining positional information of the second nucleoside triphosphate along the target nucleic acid molecule based on a change in the rotational pattern.

In some embodiments, the contacting and detecting steps under the second sequencing conditions are performed simultaneously with the contacting and detecting steps under the first sequencing conditions. In some embodiments, the contacting and detecting steps under the second sequencing conditions are performed sequentially before or after the contacting and detecting steps under the first sequencing conditions.

Such methods also can include providing a solid substrate onto which RNA polymerase is immobilized; contacting the RNA polymerase with the target nucleic acid molecule comprising the rotation tag under third sequencing conditions, wherein the third sequencing conditions comprise the presence of four nucleoside triphosphates, where a third nucleoside triphosphate of the four nucleoside triphosphates is present in a rate-limiting amount; detecting the rotational pattern of the rotation tag under the third sequencing conditions; and determining positional information of the third nucleoside triphosphate along the target nucleic acid molecule based on a change in the rotational pattern. Such methods can further include determining the sequence of the target nucleic acid molecule from the positional information for the first, second and third nucleoside triphosphates within the target nucleic acid molecule.

Such methods further can include providing a solid substrate onto which RNA polymerase is immobilized; contacting the RNA polymerase with the target nucleic acid molecule comprising the rotation tag under fourth sequencing conditions, wherein the fourth sequencing conditions comprise the presence of four nucleoside triphosphates, where a fourth nucleoside triphosphate of the four nucleoside triphosphates is present in a rate-limiting amount; detecting the rotational pattern of the rotation tag under the fourth sequencing conditions; and determining positional information of the fourth nucleoside triphosphate along the target nucleic acid molecule based on a change in the rotational pattern.

In some embodiments, the solid surface is a glass slide. Such a glass slide can be coated with Copper and PEG. In some embodiments, the RNA polymerase is a T7 RNA polymerase. In some embodiments, the T7 RNA polymerase is immobilized on the solid substrate via a His-tag.

In another aspect, a method of determining the sequence of a target nucleic acid molecule is provided. Such a method typically includes providing a solid substrate onto which one or more RNA polymerases are immobilized; contacting the one or more RNA polymerases with the target nucleic acid molecule under first sequencing conditions, wherein the target nucleic acid molecule comprises a rotation tag, wherein the first sequencing conditions comprise the presence of a first of four nucleoside triphosphates; and detecting, under the first sequencing conditions, whether a change in the rotational pattern occurs. If a change in the rotational pattern occurs, the method further comprises repeating the contacting step and subsequent steps under the first sequencing conditions, while, if a change in the rotational pattern does not occur, the method further comprises repeating the contacting step and subsequent steps under second sequencing conditions, wherein the second sequencing conditions comprise the presence of a second of four nucleoside triphosphates Similarly, if a change in the rotational pattern occurs, the method further comprises repeating the contacting step and subsequent steps under the first sequencing conditions, while, if a change in the rotational pattern does not occur, the method further comprises repeating the contacting step and subsequent steps under third sequencing conditions, wherein the third sequencing conditions comprise the presence of a third of four nucleoside triphosphates. The sequence of the target nucleic acid molecule can be obtained based, sequentially, on the occurrence of a change in the rotational pattern under the first, second, or third sequencing conditions.

In still another aspect, an article of manufacture is provided. Articles of manufacture typically include a solid substrate onto which a plurality of RNA polymerase enzymes are immobilized. In some embodiments, the solid substrate is coated with copper and PEG; in another embodiment, the solid substrate is coated with nickel and PEG. Alternatively, the solid substrate can be coated with Ni-NTA. In some embodiments, the solid substrate is a CMOS or CCD.

In some embodiments, an article of manufacture further includes a rotation tag. A rotation tag can include a non-spherical tag, or a spherical tag having a non-uniform surface that can be distinguished optically. An article of manufacture also can include T7 RNA polymerase promoter sequences and/or biotinylated nucleic acid tether sequences. Articles of manufacture as described herein also can include one or more nucleoside triphosphates.

In some embodiments, the article of manufacture further includes instructions for: identifying rotation of the rotational tag relative to an axis through the magnetic reference tag; compiling a sequence of a target nucleic acid molecule based on the rotation and the presence of a nucleoside triphosphate; or applying a magnetic force. Such instructions can be provided in electronic form.

In yet another aspect, an apparatus for single-base sequencing of target nucleic acid molecules is provided. Such an apparatus typically includes a Sequencing Module, wherein the Sequencing Module includes a receptacle for receiving a solid substrate, wherein the solid substrate comprises a plurality of RNA polymerases immobilized thereon; a source for providing directional force, wherein the directional force is sufficient and in a direction such that tension is applied to target nucleic acid molecules being transcribed by the plurality of RNA polymerases immobilized on the solid surface; a light source for projecting light onto a rotation tag bound to target nucleic acid molecules being transcribed by the plurality of RNA polymerases immobilized on the solid surface; and optics for detecting a rotational pattern of a rotation tag bound to target nucleic acid molecules being transcribed by the plurality of RNA polymerases immobilized on the solid surface.

Such an apparatus further can include a computer processor, and/or fluidics for containing and transporting reagents and buffers involved in sequencing nucleic acids. Representative reagents nucleoside triphosphates and representative buffers can be a wash buffer. In some embodiments, the source for providing directional force can be a magnet or a flow of liquid. In some embodiments, the optics comprises a microscope, and further can includes a camera.

Such an apparatus further can include a Sample Preparation Module, wherein the Sample Preparation Module includes a receptacle for receiving a biological sample; and fluidics for containing and transporting reagents and buffers involved in isolating and preparing nucleic acids for sequencing. Representative reagents include cell lysis reagents and/or cleavage enzymes, while representative buffers include lysis buffer and/or wash buffer.

Such an apparatus further can include a Template Finishing Module, wherein the Template Finishing Module includes fluidics for containing and transporting reagents and buffers involved in attaching RNA polymerase promoter sequences and rotation tags to nucleic acid molecules. Representative reagents include ligase enzyme, a molecular motor-binding sequence, a magnetic tag, and/or a tether, while representative buffers include ligase buffer, magnetic reference tag-binding buffer, and/or rotational tag-binding buffer.

In yet another aspect, a method of determining the sequence of a target nucleic acid molecule is provided, where the target nucleic acid molecules include a rotation tag, and where the sequence of the target nucleic acid molecule is based upon data obtained during transcription of the target nucleic acid molecule. Such a method generally includes receiving a first datum for a first position of the target nucleic acid molecule, wherein the first datum indicates the presence or absence of rotation and/or the length of time between rotations of the rotation tag; receiving a second datum for the first position of the target nucleic acid molecule, wherein the second datum indicates the presence and/or amount of one or more nucleoside triphosphates available during transcription; receiving another first datum and another second datum for a second position of the target nucleic acid molecule; receiving yet another first datum and yet another second datum for a third position of the target nucleic acid molecule; repeating the receiving steps of the first datum and the second datum for a fourth and subsequent positions of the target nucleic acid molecule; and determining a sequence of the target nucleic acid molecule based on the first datum and second datum received for each position. In some embodiments, the first datum and the second datum is recorded as a nucleotide at an indicated position.

Unless otherwise defined, all technical and scientific terms used herein have the same meaning as commonly understood by one of ordinary skill in the art to which the systems, methods and compositions of matter belong. Although systems, methods and materials similar or equivalent to those described herein can be used in the practice or testing of the systems, methods and compositions of matter, suitable systems, methods and materials are described below. In addition, the systems, materials, methods, and examples are illustrative only and not intended to be limiting. Any publications, patent applications, patents, and other references mentioned below are incorporated by reference in their entirety.

DESCRIPTION OF DRAWINGS

Like reference symbols in the various drawings indicate like elements.

DETAILED DESCRIPTION

Figure 1A:
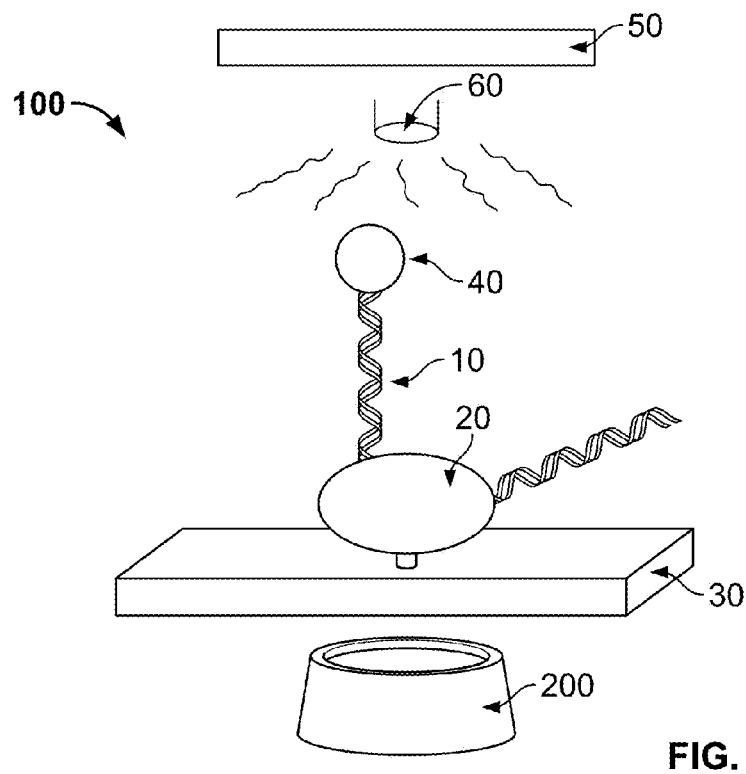
FIG. 1 shows an embodiment of a single-molecule rotation-dependent transcriptional sequencing complex (FIG. 1A) and an embodiment of on-chip (FIG. 1B) rotation-dependent transcriptional sequencing complexes, as described herein.

The present disclosure describes a single molecule sequencing system in which many of the constraints of existing single molecule system are relaxed, including complexity, cost, scalability and, ultimately, longer read lengths, higher throughput and enhanced accuracy. The real time, single molecule sequencing method and system described herein can sequence thousands of nucleotides in a very short time with high accuracy due to highly processive transcriptional machinery and simple optical and imaging systems.

The advantages of the present system are numerous. For example, double stranded nucleic acid is used as the template, which minimizes and limits the requirements for sample preparation. In addition, labeled nucleotides are not required, since very simple imaging methods can be used (e.g., CMOS), which significantly reduces the cost. Also, wild type RNA polymerase enzymes can be used; no special modifications to the enzyme are necessary, and the surface chemistry and enzyme immobilization technologies are routine. The present systems and methods are suitable for homopolymeric sequences, since rotation is the same for each nucleotide and, thus, is cumulative over multiple nucleotides. The present systems and methods also are readily adaptable for high throughput sequencing.

Overview of Rotation-Dependent Transcriptional Sequencing

Rotation-dependent transcriptional sequencing relies upon transcription of target nucleic acid molecules by RNA polymerase. The RNA polymerase is immobilized on a solid surface, and a rotation tag is bound to the target nucleic acid molecules. During transcription, RNA polymerase establishes a transcription bubble in the template nucleic acid that contains within it an RNA:DNA hybrid of approximately 8 bases. As the RNA polymerase advances along the double-stranded nucleic acid template, it must unwind the helix at the leading edge of the bubble and reanneal the strands at the trailing edge. The torque produced as a result of the unwinding of the double-stranded helix results in rotation of the template nucleic acid relative to the RNA polymerase of about 36° per nucleotide incorporated. Therefore, when the RNA polymerase is immobilized on a solid surface and a rotation tag is attached to the template nucleic acid, the rotation of the template nucleic acid can be observed and is indicative of transcriptional activity (i.e., incorporation of a nucleoside triphosphate) by the enzyme.

As described herein, the sequence of target nucleic acid molecules are determined or obtained based upon changes in the rotational pattern of a rotation tag. Also as described herein, detecting the presence or absence of rotation of the nucleic acid can be done, for example, using illumination of the rotation tag bound to the target nucleic acid molecules. The rotational sequencing methods described herein can be scaled up for whole genome sequencing using an array of RNA polymerase enzymes and any number of routine imaging methods suitable for capturing the rotation of the rotation tag.

Figure 1B:
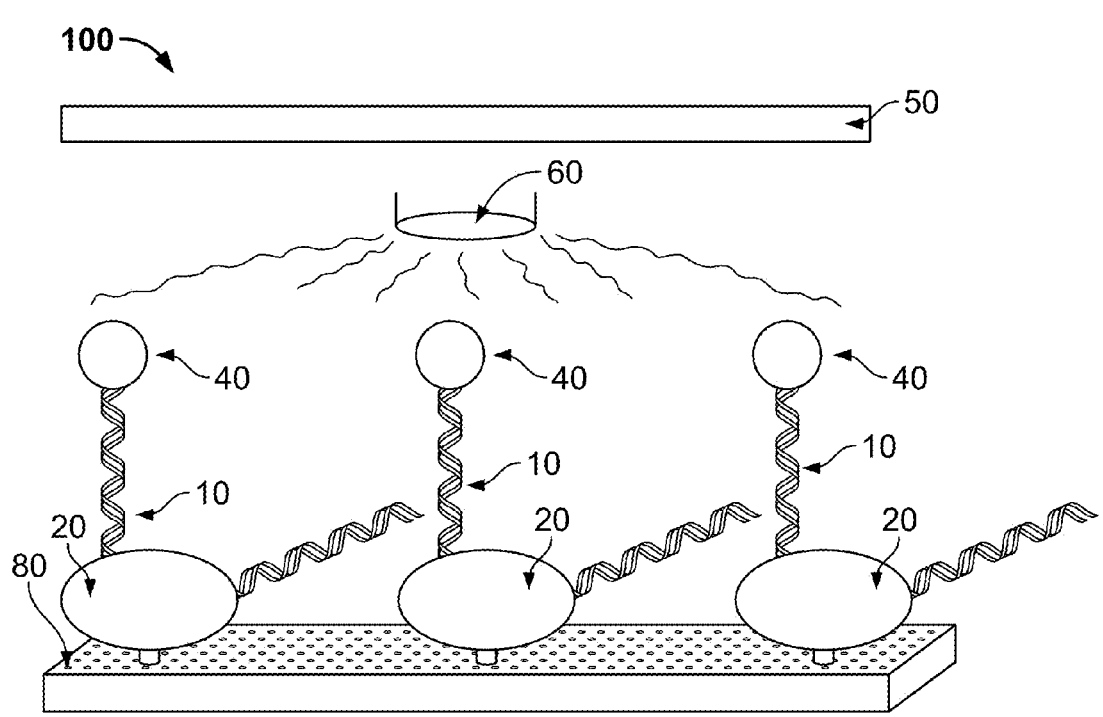

FIG. 1 shows a single-molecule sequencing embodiment (FIG. 1A) and an on-chip array embodiment (FIG. 1B) of the rotation-dependent transcriptional sequencing complex described herein. The rotation-dependent transcriptional sequencing complex described herein can be used to determine the sequence of a target nucleic acid molecule 10. In some embodiments, RNA polymerase 20, immobilized on a solid surface 30 or on a chip 80, is contacted with a target nucleic acid molecule 10 (i.e., a nucleic acid molecule having an unknown sequence). According to the methods described herein, the target nucleic acid molecule 10 includes a rotation tag 40. Under particular sequencing conditions, which include the presence of at least one nucleoside triphosphate, changes in the movement and/or velocity of the rotation tag 40 create a rotational pattern. These steps are repeated multiple times, and the sequence of the target nucleic acid is determined based, sequentially, on the presence or absence of a change in the rotational pattern under the particular sequencing conditions. These features are discussed in more detail below.

Solid Surface

For the rotation-dependent transcriptional sequencing described herein, an RNA polymerase is immobilized on a solid surface. In the embodiments described herein, a solid surface typically is made from a silica-based glass (e.g., borosilicate glass, fused silica, or quartz). Solid surface materials for single molecule imaging are well known and routinely used in the art, and the same solid surface materials used for single molecule imaging also can be used in an array format. However, other materials (e.g., polypropylene, polystyrene, silicon, silicon nitride, and other polymers or composites thereof) also can be used provided they are suitable for use in the sequencing described herein. FIG. 1B shows an "on-chip" embodiment, where the solid surface 30 also includes the detection system. These types of solid surfaces (e.g., CMOS and CCD) are also known in the art and are discussed in more detail below.

Before immobilizing one or more biological molecules into a solid surface, the solid surface generally is modified (e.g., functionalized) to receive and bind the biological molecules. Methods of functionalizing solid surfaces for immobilizing biological enzymes are known in the art. In some embodiments, the solid surface can be functionalized with copper or nickel, while in some embodiments, the solid surface can be functionalized with Ni-NTA (see, for example, Paik et al., 2005, Chem. Commun. (Camb), 15:1956-8) or Cu-NTA. Alternatively, metals such as cobalt or the like can be used to modify a solid surface for immobilization.

Prior to modifying a solid surface, the solid surface can be treated with, for example, PEG moieties. Such strategies can be used to regulate the density of RNA polymerases on a solid surface, and also can be used to generate a pattern of RNA polymerases on the solid surface, such as a uniform, a semi-ordered or a random array of RNA polymerases. The PEG environment results in minimal interactions between the enzyme and the surface (except for the binding tag on the N- or C-terminus), and ultimately results in minimal disturbance to the native conformation of the immobilized enzyme. In addition, surface passivation methods are known in the art and can include, for example, treating the solid surface with bovine serum albumin (BSA).

RNA Polymerase

The rotation-dependent transcriptional sequencing methods described herein are based on the action of RNA polymerase during the process of transcription and the rotational force produced on the transcribed nucleic acid (see, for example, US 2007/0077575). While multi-subunit RNA polymerases (e.g., E. coli or other prokaryotic RNA polymerase or one of the eukaryotic RNA polymerases) can be used in the sequencing methods described herein, the small, single-subunit RNA polymerases such as those from bacteriophage are particularly suitable. Single subunit RNA polymerases or the genes encoding such enzymes can be obtained from the T3, T7, SP6, or K11 bacteriophages.

The bacteriophage RNA polymerases are very processive and accurate compared to many of the multi-subunit RNA polymerases, and often produce fewer deletion-insertion errors. Additionally, RNA polymerases from bacteriophage are significantly less prone to back-tracking compared to multi-subunit counterparts such as the RNA polymerase from E. coli. RNA polymerase from several different bacteriophages has been described. Simply by way of example, the T7 RNA polymerase is made up of a single polypeptide having a molecular weight of 99 kDa, and the cloning and expression of the gene encoding T7 RNA polymerase is described in U.S. Pat. No. 5,693,489. The structure of T7 RNA polymerase has been resolved to a level of 3.3 Angstroms, with four different crystal structures having been solved: T7 RNA polymerase alone (uncomplexed), T7 RNA polymerase bound to a nucleic acid promoter, the entire initiation complex (T7 RNA polymerase bound to a nucleic acid promoter and one or more transcription factors), and T7 RNA polymerase bound by an inhibitor.

RNA polymerases that are suitable for use in the methods described herein typically provide rotations of the nucleic acid having durations in the range of sub-microsecond to 100 milliseconds for every nucleotide incorporated into the transcript, but RNA polymerases that provide rotations having durations in the range of 100 milliseconds up to several seconds per nucleotide also can be used. It would be understood by those skilled in the art that, in order to produce the necessary rotation, the RNA polymerase must transcribe double-stranded nucleic acid.

The density and/or distribution of RNA polymerases on a solid surface can be controlled or manipulated, for example, to optimize the particular sequencing reactions being performed. As is known in the art, an array of biological molecules can be generated in a pattern. For example, an array of biological molecules can be randomly distributed on the solid surface, uniformly distributed or distributed in an ordered or semi-ordered fashion. In some embodiments, a solid surface can have greater than 100 RNA polymerases, or greater than 1000 RNA polymerases (e.g., greater than 10,000 RNA polymerases) immobilized thereon. In some embodiments, a solid surface can have at least one RNA polymerase immobilized per ~5 $\mu m^2$ (e.g., at least one RNA polymerase immobilized per ~2.5 $\mu m^2$, ~1 $\mu m^2$, ~0.5 $\mu m^2$, or ~0.1 $\mu m^2$). It would be understood that the density of RNA polymerases on a solid surface may depend, at least, in part, upon the size of the target nucleic acid molecules being sequenced as well as the particular rotation tag utilized.

While the sequencing methods described herein rely upon the rotation created during transcription by RNA polymerase, other molecular motors can be used in conjunction with RNA polymerase to create rotation. Molecular motors are biological molecules that consume energy, typically by hydrolysis of a nucleotide triphosphate, and convert it into motion or mechanical work. Examples of molecular motors include, without limitation, helicases, topoisomerases, DNA polymerases, myosin, ATPases and GTPases. In some embodiments, a molecular motor can be immobilized on a solid surface and transcription by RNA polymerase can occur at a position on the target nucleic acid molecule between the molecular motor and the rotation tag. In such instances, the rotational pattern would be a result of any rotational force placed on the nucleic acid molecule by the molecular motor combined with the rotational force placed on the nucleic acid molecule by the RNA polymerase. As an alternative to an enzymatic molecular motor, a solid state MEMS motor, for example, can be used, in conjunction with RNA polymerase, to generate rotation.

RNA polymerase can be immobilized on a solid surface using any number of known means. For example, in one embodiment, the RNA polymerase contains a His-tag (e.g., His tags having 4 His residues, 6 His residues, or 10 His residues). A His-tag or other suitable tag can be used provided it is compatible with the surface chemistry (e.g., functionalization) discussed above.

Target Nucleic Acid Molecules

Nucleic acid molecules for rotation-dependent transcriptional sequencing can be obtained from virtually any source including eukaryotes, bacteria and archaea. Eukaryotic nucleic acids can be from humans or other mammals (e.g., primates, horses, cattle, dogs, cats, and rodents) or non-mammals (e.g., birds, reptiles (e.g., snakes, turtles, alligators, etc.) and fish), while prokaryotic nucleic acids can be from bacteria (e.g., pathogenic bacteria such as, without limitation, *Streptococcus, E. coli, Pseudomonas,* and *Salmonella*) or Archaea (e.g., Crenarchaeota, and Euryarchaeota).

Nucleic acid molecules for rotation-dependent transcriptional sequencing can be contained within any number of biological samples. Representative biological samples include, without limitation, fluids (e.g., blood, urine, semen) and tissues (e.g., organ, skin, mucous membrane, and tumor).

As discussed herein, one of the advantages of the rotation-dependent transcriptional sequencing methods described herein is that double-stranded nucleic acid is used as the template. This reduces the need to manipulate the sample and the nucleic acid, which is a significant advantage, particularly when sequencing nucleic acids greater than 1 Kilobase (Kb; e.g., greater than 2 Kb, greater than 5 Kb, greater than 10 Kb, greater than 20 Kb, or greater than 50 Kb) in length, since many methods used to obtain nucleic acids from biological samples result in undesired cleavage, shearing or breakage of the nucleic acids. Obviously, single-stranded nucleic acids (or samples containing single-stranded nucleic acids) can be used in the present methods. However, such single-stranded nucleic acids must be converted into a double-stranded nucleic acid in order to exhibit rotation during transcription. Methods of making double-stranded nucleic acids are well known in the art and will depend upon the nature of the single-stranded nucleic acid (e.g., DNA or RNA). Such methods typically include the use of well known DNA polymerases and/or Reverse Transcriptase enzymes.

Sample preparation will be dependent upon the source, but typically will include nucleic acid isolation followed by promoter ligation. Nucleic acid templates used in the sequencing methods described herein do not require any special preparation and, thus, standard DNA isolation methods can be used. Finally, a promoter sequence that is recognized by the particular RNA polymerase being used in the transcriptional sequencing system must be ligated to the target nucleic acid molecules. Promoter sequences recognized by a large number of RNA polymerases are known in the art and are widely used. In addition, methods of ligating one nucleic acid molecule (e.g., a promoter sequence) to another nucleic acid molecule (e.g., a target nucleic acid molecule having an unknown sequence) are well known in the art and a number of ligase enzymes are commercially available.

In addition, isolated nucleic acids optionally can be fragmented and, if desired, particular sizes can be selected or fractionated. For example, isolated nucleic acids can be fragmented using ultrasonication and, if desired, size-selected using routine gel electrophoresis methodology.

In addition, the target nucleic acids optionally can be circularized into, for example, a plasmid, so that sequencing can be performed on a circular target in a repetitive or recursive fashion.

Rotation Tags

For the rotation-dependent transcriptional sequencing methods described herein, the target nucleic acid molecule being sequenced includes a rotation tag bound thereto. Such a tag is fixed to the nucleic acid such that it rotates under the torque imparted on the nucleic acid by the RNA polymerase. Rotation tags can be as large as many microns (e.g., greater than 1 micron, 2 microns, 3 microns or 5 microns) in diameter and as small as nanometers (e.g., about 50 nm, 100 nm, 250 nm, 500 nm, 750 nm, 850 nm, or 950 nm) in diameter. As used herein, a rotation tag can be non-spherical or spherical; however, if the rotation tag is a single sphere, it must have some non-uniform feature that can be used to detect rotation.

A non-spherical tag can include a single moiety that is not a sphere (e.g., a tapered rod, triangular, conical, or egg-shaped). In addition, a non-spherical tag can be made using two (or more) different size spherical tags (e.g., a first tag attached to a second tag) that, together, provide an asymmetry that allows detecting of rotation. In some embodiments, the first and second tags can be the same or essentially the same size. For example, the first tag, tethered to the target nucleic acid molecule, can be considered the reference tag, while the second tag, attached to the first tag, can be considered the rotation tag. In some embodiments, the first tag, tethered to the target nucleic acid molecule, is larger while the second tag, attached to the first tag, is smaller. This configuration places the second tag as far as possible from the point of rotation of the first tag, which enhances the resolution of the rotation under optical detection. Thus, the size of the smaller tag has to be large enough for detection purposes but small enough to minimize the hydrodynamic effects due to the size of the overall rotation tag.

For example, in some embodiments, a rotation tag can include a larger bead (e.g., from about 1 micron up to about 3 microns in diameter) as a first tag and a smaller bead (e.g., from about 0.5 microns up to about 1 micron in diameter) as a second tag. For example, the larger bead can be 0.75 or 1 micron and the smaller bead can be 0.5 micron. These sizes are adequate to resolve rotation (using, as described in more detail below, for example, an optical system that includes a 50× magnification Mitutoyo objective with numerical Aperture of 0.75 in combination with a 1× tube lens and a scientific CMOS camera of 6.5 micrometer pixel size or smaller). In some embodiments, a first tag can be 0.75 microns in diameter and a second tag can be 0.35 microns in diameter. These sizes also are adequate to resolve rotation (using, as described in more detail below, for example, a 100× objective with a numerical aperture of 0.9 or higher using a scientific CMOS camera).

An attachment between, e.g., a first tag and a second tag can be a mechanical tether or linkage (e.g., streptavidin-biotin bond), a chemical bond (e.g., amine or carboxy), a magnetic attraction, or any combination thereof. In some embodiments, a first tag and a second tag can be physically attached to one another through, for example, a polymerization reaction.

On the other hand, a rotation tag can be spherical provided that its rotation can be detected. The use of a rotation tag that is spherical reduces or eliminates the non-linear dynamics created by a non-spherical rotation tag, and a spherical rotation tag will exhibit lower hydrodynamic resistance during rotation than a non-spherical rotation tag. One example of a spherical tag having a non-uniform feature that can be used to detect rotation is a Janus bead. See, for example, Casagrande et al. (1989, *Europhys. Lett.* 9:251). A Janus bead refers to a spherical bead in which one hemisphere is hydrophobic and the other hemisphere is hydrophilic, due to a nickel coating on half of the sphere. The different features of the hemispheres allows for detecting rotation, even when the rotation tag is spherical.

In some embodiments discussed herein, a rotation tag can be magnetic. Magnetic tags, spherical or non-spherical, are well known in the art and can be in the form of magnetic beads, rods, or other magnetic moieties such as, without limitation, superparamagnetic particles. The entire rotation tag can be magnetic, or only a portion of the rotation tag can be magnetic. For example, in some embodiments, only the first tag of a rotation tag can be magnetic. There are a number of commercial sources for magnetic tags. The following paragraphs describe a number of ways in which a magnetic rotation tag can be generated for use in the sequencing methods described herein.

In some embodiments, a nanomagnetic solution (e.g., 1% w/v in toluene or xylene with Cobalt, or Fe3o4 or FePt in toluene or xylene) can be applied to ordinary polymeric beads to make them magnetic. In some embodiments, the nanomagnetic materials can be applied to half of the surface of the polymer bead. This results in a magnetic bead whose halves exhibit a different index of refraction or other optical property (e.g., scattering). In some embodiments, superparamagnetic particles (or half of the particle) can be coated with nanosilver ink to create optically reflecting, yet fully superparamagnetic beads. In these embodiments, deposition and evaporation processes can be used with such "inks" (e.g., PRIMAXX) to impart particular optical properties on magnetic particles or portions of magnetic particles. In some embodiments, superparamagnetic particles (or half of the particle) can be coated with quantum dots to impart particular optical properties on particles that already are magnetic. In some embodiments, magnetochromic particles can be used as rotation tags. Within magnetochromic particles, nanomagnets form chains within polymers or encapsulated in Carbon shells. The chains of nanoparticles are aligned with respect to each other using an external magnetic or electromagnetic field. When light scatters from the particle, the aligned chains act as Bragg diffraction gratings and scatter light in appropriately defined directions. The magnetochromic particles rotate inside an external field such that intensity modulation can be monitored between the stopped particle with all chains aligned and the particle in rotation where the chains are not completely aligned to determine the rotation duration from a starting position to a resting or stopping position until the next rotation.

In some embodiments, a first magnetic tag can be combined with a second tag that can induce an electric field change onto a detector. Such electric tags are known in the art and can be polymeric spheres that include metallic elements, are charged, or are micron-sized radiofrequency oscillators that induce a change in the magnetic or electric field, which can be captured on an instrument (described in more detail below).

Simply to provide a spatial perspective and without being bound by any particular size or distance limitation, the bottom surface of a rotation tag, even when a 10 Kb nucleic acid molecule is being transcribed, still may only be 3 µm from the top of the solid surface. That is, the rotation tag is very close to the solid surface even at the beginning of transcription. At the end of transcription, the rotation tag could be nearly contacting the RNA polymerase enzyme, and so separated from the top of the solid surface by a very small distance. In other words, a rotation tag that has a diameter of 2 µm will be approximately the same size as the nucleic acid molecule being transcribed. It would be understood by those in the art that transcription of the target nucleic acid molecules by RNA polymerase could proceed in the opposite direction, thereby moving the rotation tag farther away from the solid surface during transcription.

Rotation tags can be attached to target nucleic acid molecules using tethers. Tethers to attach rotation tags to target nucleic acid molecules are known in the art and include, without limitation, a chemical linkage (e.g., crosslinking, van der Walls or hydrogen bond) or a protein linkage (e.g., biotin-streptavidin binding pairs, digoxigenin and a recognizing antibody, hydrazine bonding or His-tagging). For example, in some embodiments, a rotation tag can be coated, at least partially, with streptavidin, while a biotinylated nucleic acid tether can be ligated to the target nucleic acid molecules. In some embodiments, a biotin-labeled nucleic acid (e.g., about 500 base pairs (bp)) can be ligated to one end of the target nucleic acid molecules. The target nucleic acid molecules having the biotin-labeled tether then can be combined with streptavidin-coated rotation tags. There are a number of commercially available tags, including magnetic tags that are coated or partially coated with various chemistries that can be used to tether the target nucleic acid molecules and/or bind a second tag (e.g., Dynal, Invitrogen, Spherotech, Kisker Inc., Bangs Laboratories Inc.).

Tension on the Nucleic Acid Molecules

In some embodiments, the rotation-dependent transcriptional sequencing methods described herein include applying a directional force on the target nucleic acid molecules, which results in the target nucleic acid molecules being placed under some amount of tension. Tension on the target nucleic acid molecules becomes important with longer target nucleic acid molecules, as longer nucleic acid molecules can fold-up or collapse on themselves. Any type of abnormal helical structure of the target nucleic acid molecules could dampen or mask the torque transferred from the RNA polymerase to the rotation tag.

The directional force applied to the target nucleic acid molecules needs to be sufficient so as to maintain the double-stranded helical nature of the target nucleic acid molecule, particularly downstream of the transcription complex, and particularly when the rotation tag is thousands or hundreds of thousands of nucleotides away from the RNA polymerase. However, the directional force applied to the target nucleic acid molecules can't be so strong (i.e., apply so much tension) such that rotation of the rotation tag is impeded in any way or the backbone of the target nucleic acid molecule breaks. Such tension on the target nucleic acid molecules also can reduce the Brownian motion of the rotation tag or other noise effects (e.g., thermofluidic noise effects), thereby increasing the accuracy of detecting the rotational pattern of the rotation tag.

The tension is intended to elevate the nucleic acid-tethered rotation tag up and away from the surface in a prescribed amount of force and location in the three-dimensional space. The direction of the tension can extend the target nucleic acid in essentially a 90° angle (i.e., in the z-axis) relative to the plane of the solid surface (i.e., in the x-axis), but the directional force also can extend the target nucleic acid molecules in a direction that is more or less than 90° relative to the plane of the solid surface. It would be understood, however, that the rotation tag cannot be so near the solid surface that the surface (e.g., due to surface chemistry or surface fluidic phenomena) interferes with (e.g., changes, alters, dampens, reduces, eliminates) the torque profile and/or the pattern of movement of the rotation tag as a signal of RNA polymerase activity.

In some embodiments, the tension source (or the source of the directional force) can be a magnet. In such cases, the rotation tag or a portion of the rotation tag can be magnetic. As indicated herein, magnetic tags (e.g., beads, rods, etc.) are well known in the art. For example, a magnetic force can be applied that provides a uniform spatial force in the direction of the z-axis at a magnitude of, for example, about 1 pN, to adequately stretch the target nucleic acid molecules and avoid any looping. At the same time, such magnets generate only a miniscule force in the direction of the x-axis. These features allow the rotation tags to freely rotate, while stabilizing any Brownian motion of the rotation tags. In some embodiments, the tension source can be a result of a directional flow of, for example, liquid (e.g., water or buffer) or air.

The amount of tension applied to the target nucleic acid molecules can be calibrated using standard fluidic methodology and incorporated in data acquisition and analysis process or base calling algorithms. For example, such a calibration can include monitoring the Brownian motion of a rotation tag, attached to a nucleic acid molecule being transcribed by a RNA polymerase, which is immobilized on the surface, at various locations above the surface, at various angles relative to the plane of the surface, and/or in different flows or magnetic fields.

Simply to provide a spatial perspective and without being bound by any particular size or distance limitation, in an on-chip embodiment, the rotation tag can be on the order of 1 micron above the surface when tension is applied. For example, since each base is separated by 0.3 nm from the next base, a one Kb nucleic acid molecule that is attached at the surface to the RNA polymerase will have the rotation tag on the other end at a distance of about 300 nm from the surface. This distance can be varied using, without limitation, different immobilization methods of the RNA polymerase to the solid surface and nucleic acids (e.g., promoter sequences, tether sequences) of different lengths. The rotation-dependent transcriptional sequencing described herein can accommodate situations in which the rotation tag is from 10 nm to many microns from the surface.

Figure 2A:
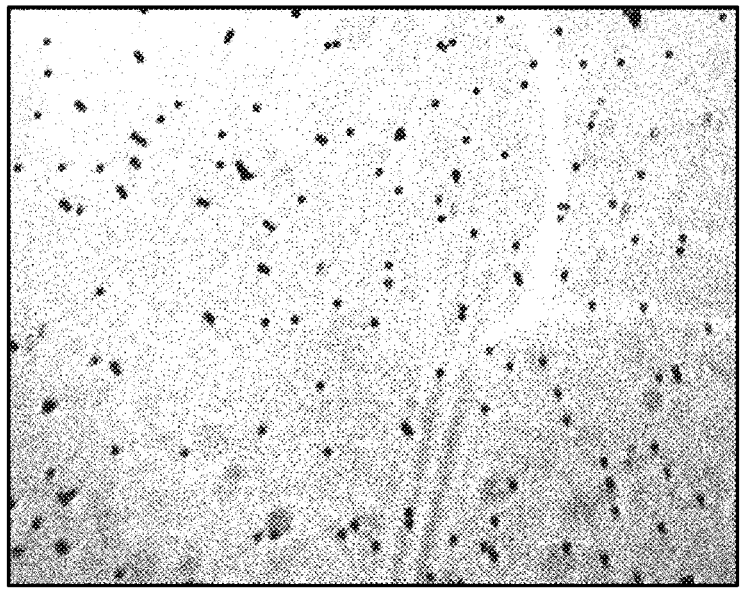
FIG. 2A is an image of magnetic rotation tags using a 20× water objective. In this image, the FOV is limited by the detector and not by the objective. In this image, the magnetic rotation tags have a diameter of 2.7 microns.
Figure 2B:
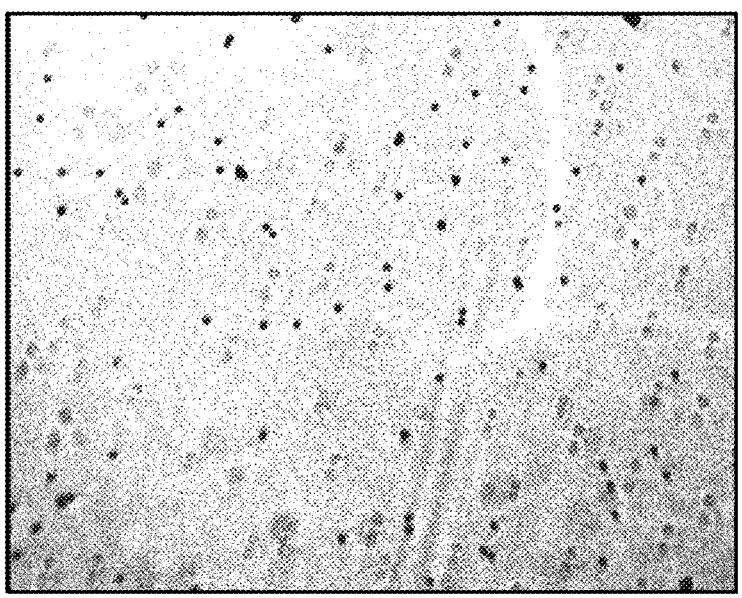
FIG. 2B is an image of magnetic rotation tags under tension (here, in the presence of a magnetic force), which shows, compared to FIG. 2A, that the magnetic rotation tags have moved "upwards" due to application of the magnet. The double-images are created due to the presence of two light sources illuminating the rotation tag from above at two different angles. Therefore, when rotation tags move out of the focal plane, the two "shadows" separate. This method can be used to determine how uniform the tension is in the plane of the sample and in different z-axis locations out of the plane. The rotation tags that are still in-focus in FIG. 2B are likely clumped on the solid surface.

FIG. 2 shows 2.7 micron magnetic beads before (FIG. 2A) and after (FIG. 2B) application of a magnetic field.

Detection Methods

Detecting the rotational pattern of the rotation tag under various sequencing conditions in the rotation-dependent transcriptional sequencing methods described herein requires a light source, for projecting light onto the rotation tag, and optics, for visualizing the rotation tag and observing changes in the rotational pattern. While any number of suitable illumination methods and optics can be used in the rotation-dependent transcriptional sequencing methods described herein, the following embodiments are provided as examples of the simplicity of the present systems and methods and the lack of any requirement for complex and expensive technologies for the detection component.

The light source can be LED, or the light source can be white light or single- or multi-fibers. The light source can be steady illumination or can be provided as pulsed illumination, if desired. The light can be projected from the same direction or from multiple directions. For example, the light source can be polymer fibers or bundles, which can be tunable (e.g., in intensity and/or spectrum). Fresnel and/or Fraunhoffer diffraction can be used, based on the size of the rotation tag and its distance from the detector, to identify the rotation tag (e.g., the shape of the rotation tag) and identify its rotation.

The optics can be simple lenses and objectives (e.g., a microscope lens with a 50× objective, e.g., Mitutoyo 50× with numerical aperture of 0.75) and a tube lens with 1× magnification. The optics also can include a camera (e.g., a video camera, e.g., a scientific CMOS) operating at appropriate frames per second. Alternatively, the optics can utilize current complementary metal-oxide-semiconductor (CMOS) or charge-coupled device (CCD) technology, provided they have an adequate number of pixels (and provided the light source provides sufficient photons to image the rotation of the rotation tag). Currently used CMOS detectors are very fast (e.g., 1000 or more frames per second, corresponding to exposures of 1 ms or less). This level of detector speed removes any ambiguity due to the stochastic nature of rapid nucleotide incorporation that plagues current approaches. For example, many current approaches (e.g., Pacific Biosciences, Complete Genomics, Inc.) are typically limited to exposures of 10 ms or longer, due to the need to collect an adequate number of fluorescent photons within the camera exposure window, which results in errors in the sequence data collected.

The ability to use a small pixel size for the imaging detector is another advantage of the present methods compared to other sequencing technologies (e.g., Pacific Biosciences, Complete Genomics Inc., and others that rely upon single-molecule fluorescence or general fluorescence at high throughput image capture). The rotation-dependent transcriptional sequencing described herein can use a small pixel size (e.g., 1.4 microns, which is the current state of the art for cell phone cameras), compared to the 6.5 microns, which is the state of the art for the CMOS sensors used in other real-time sequencing applications. This is primarily because the current sequencing methods can accommodate more noise than other systems. Significantly, in the rotation-dependent transcriptional sequencing described herein, the throughput of imaging can be much higher because of the ability to use large sensors having small pixels (e.g., 8-10 MPixels common in next-generation cell phones) and by imaging a larger area of the surface. The detection methods for the rotation-dependent transcriptional sequencing methods described herein allow for the use of commercial CMOS camera hardware with only modifications to the software, as opposed to other sequencing systems in the industry, which rely upon specialized optical platforms (e.g., ChemFet, Ion Torrent).

The data acquisition method in video mode from these sensors typically uses the intensity value of each pixel (e.g., using RAW format data). When the light source is a white LED or an RGB illuminator with appropriate balancing between the colors, diffraction and shadow patterns of a rotation tag will be recorded in adjacent pixels and an image can be generated as if the sensor was a black and white sensor. For example, direct shadow or diffraction of, for example, a non-spherical rotation tag, can be recorded on the detector's pixels and rotation can be detected due to the changing effects on diffraction.

Simply by way of example, detection of rotation (e.g., detection of the pattern of rotation by a rotation tag) can occur as follows. Rotation tags can be illuminated from above using, for example, an LED or fiber coupled—LED or LED array. Below the solid surface flow cell, a Mitutoyo 50× objective having a numerical aperture of 0.75 that is infinity corrected can be used in conjunction with a tube lens that images the field of view onto a scientific CMOS chip (e.g., having 5.5 MP, with a 6.5 micron center-to-center distance between pixels that are approximately 6.5 micron size each). Assigning 10×10 pixels to each rotation tag, such a pixel size is adequate to detect rotation of 1 micron beads, which, on the entire CMOS surface, can result in more than 55,000 rotation tags. If each rotation tag is attached to a 5 Kb target nucleic acid molecule, the rotation-dependent transcriptional sequencing described herein can sequence more than 275 Mbases in a single run on a single chip. By way of comparison, the *E. coli* genome is 4.5 Mbases. If the rate of transcription is 10 nucleotides per second, which is a reasonable number for immobilized RNA polymerase, the complete *E. coli* genome could be sequenced as described herein in 500 seconds, i.e. less than 10 minutes. A detector that has the ability to record up to 100 frames per second (i.e., 10 frames per each transcribed nucleotide) is sufficient for the sequencing systems and methods described herein. The calculations above do not include any efficiency of attachment. In addition, in an asynchronous pattern of sequencing, assuming the pause by RNA polymerase is less than 10 frames, it does not add any extra reaction time to the calculation above, however, the asynchronous pattern of sequencing could add time to the reaction if the rate-limiting nucleoside triphosphate is tuned to much lower levels (e.g., to increase accuracy and minimize deletion errors).

Another example of detecting the rotational pattern of the rotation tag follows. Rotation tags can be illuminated using an LED or fiber coupled—LED or LED array, where the rotation-dependent transcriptional sequencing complexes are placed on top of a tapered waveguide having a 350 nm core size on one side and a 6.5 micron core size on the other (about a 1:19 taper), which can be bonded to the surface of a scientific CMOS chip (e.g., Fairchild Imaging). Such a chip has 5.5 MPixels with 6.5 micron center-to-center distance between pixels that are each approximately 6.5 microns. In this case, assigning 3×3 pixels to each rotation tag, which is adequate to detect rotation of a 1 micron bead on top of the 350 nm cores, allows for more than 610,000 rotation tags on such a chip. If each rotation tag is attached to a 5 Kb target nucleic acid molecule, a total of more than 3 Gbases can be sequenced in a single run on a single chip. This is essentially single coverage of the entire human genome. The calculations above do not take into account efficiencies of attachment, the rounding effects of the signal from the round cores of the taper to the square pixels, or the loss of pixels due to mismatch in the bonding process of core-to-pixel.

The following is an example of detection of a rotational pattern in a high throughput sequencing system. For example, instead of using the tapered waveguide and scientific CMOS sensor described in the above example, an OmniVision Inc. chip with, for example, 14.5 MP and 1.2 microns per pixel, can be used after having removed the detector window and attached one or more components of the rotation-dependent transcriptional sequencing complexes directly on the microlens array of the chip. The rotation pattern using 2.8 micron rotation tags can be detected on 2×2 pixels using signal processing of videos. Allowing for an extra 2 pixels in each direction for an array of rotation tags in proximity to each other, 8 pixels total can be assigned per rotation tag. In this case, a single chip can have more than 1.8 million rotation tags attached to target nucleic acid molecules being sequenced. Therefore, three of these chips would be adequate to sequence the complete human genome, while four chips could significantly increase the accuracy. Electronics to produce a readout of this sensor in adequate speeds (e.g., to match the nucleotide incorporation rate for the specific chip) based on FPGA or other DSP designs and direct storage to arrays of solid state drives can be used and their components are known in the art.

Simply by way of example, detection of rotation can occur as follows. LED structured illumination (e.g., Lightspeed genomics module adapted for speckle-free excitation with a 4× lens) can be used to create a diffractive shadow of a rotation tag on the surface of a SciCMOS camera (e.g., 5.5 MP at 100 frames per second). The interference pattern can exploit 5 frames per image in order to enhance resolution by 9×, effectively creating a 49 MP sensor at 20 fps. Each single molecule can be assigned, for example, to a 5×5 pixel, which allows for about 2 million rotation tags per chip. Assuming Poisson efficiencies at the tag-to-tag coupling, 660,000 available single RNA polymerase molecules each transcribing 5 Kb nucleic acid molecules results in 3.3 Gbases that can be sequenced in a single run. In the asynchronous sequencing method, four reactions can be performed (although, in some embodiments, three reactions are performed and the fourth nucleotide is inferred from the sequencing information obtained with the other three nucleoside triphosphates). Allowing for 5 frames per enzyme pause with a total of 250 ms at each pause, while the polymerase otherwise incorporates 15 nt per second, throughput is an extreme 18 Gb per hour. This sequencing rate is significantly higher than any current technologies, even for short read lengths. As indicated herein, current cell phone camera technology (10 MP, 1.2 μm pixel size) meets the requirements of this system.

Similarly, color (e.g., with RGB filter coatings on the sensor) or monochrome cell phone or digital camera sensors meet the requirements for use in the sequencing methods and systems described herein (e.g.; 14.5 MP and a 1.25 micron pixel sensor). Even though each pixel of an RGB sensor is coated with a red or green or blue filter in a pattern, those sensors can be used in the sequencing systems and methods described herein since the light source used in the sequencing systems and methods described herein can have a broad spectrum (e.g. white LED(s)) and provide scattered, reflected, diffracted or transmitted optical signal to the detector portion of the camera chip (e.g. silicon).

In this example, the number of pixels used to detect each rotation tag can be estimated by the shadow or diffraction of the rotation tag. When direct light illumination is used instead of fluorescence excitation, thick optical filters that block the excitation light and/or have fluorescence passbands are not necessary. These filters can be hundreds of microns thick, which can complicate the optical designs needed to collect the fluorescence on a small number of pixels on the on-chip detector. Collecting the light on a small number of pixels is important since one aspect of the throughput of sequencing systems is defined by the total number of pixels on the detector divided by the number of pixels assigned to each site or event. For example, with an i-Phone-style 8 MP CMOS sensor, assigning 10 pixels per site, allows for a total of 800,000 sites. If a 1 Kb nucleic acid, on average, is sequenced per run per site, then, at most, throughput is 800 MBases per run. Using Fraunhoffer diffraction and 3 micrometer beads at a distance of 1 micrometer, then less than 10 pixels per site can be used without the need for lenses having complicated optical designs.

In one embodiment, a source of tension can be provided that allows for an array of rotation tags to be elevated from the surface to an area, for example, greater than 4×4 mm$^2$. The present methods and systems are not limited by the field of view (FOV), particularly when the sequencing is performed on-chip, where the effective FOV is the entire area of the chip. For example, the surface area of the Omnivision 14 MP sensor is about 6×4 mm.

As indicated herein, one of the many advantages provided by the rotation-dependent transcriptional sequencing methods described herein is the extremely fast nucleotide incorporation by RNA polymerases due to their stochastic nature. The high rate of incorporation and the resulting speed of rotation, however, can make data capture challenging. It would be understood by those skilled in the art that, in the presently described asynchronous sequencing methods, for example, only the "end-point" information needs to be recorded, e.g., only the number of total rotations until a pause occurs. That is, there is no need to capture the individual incorporation steps, which may be very fast and difficult for a simple detector to image effectively. Therefore, as long as a sequencing reaction is recorded at a high enough frame rate to detect the total amount of rotations between pauses by the RNA polymerase (due to the presence of a nucleoside triphosphate in a rate-limiting amount), an accurate nucleic acid sequence can be determined.

In some embodiments, the rotational pattern of a magnetic rotation tag can be captured using a GMR (giant magneto-resistance) array as the sensor. In some embodiments, a spin-valve array or MRAM can be used to detect the rotational pattern of a magnetic rotation tag. For example, a computer memory array (e.g., RAM, e.g., DRAM) can be modified (e.g., polished to remove layers from the surface that may be shielding the magnetic field effects) to accept a surface modification close to the memory cell capacitive elements. The induced electric field of a magnetic rotation tag can be sensed by the two-dimensional array of cells/capacitors of the RAM. The cells of the RAM array then can be read directly using memory reading software following installation of the memory into a computer. In the case when MRAM is used as a sensor, flow can be used to provide a source of tension to the target nucleic acid without the use of a magnetic field. Alternatively, a magnetic field can be used as the source of tension in a field where the sensing signal of the MRAM cells is modified.

Sequencing Conditions

Referring again to FIG. 1A, the rotation-dependent transcription complex 100 can be generated in a number of different fashions. For example, promoter-bound target nucleic acid molecules 10 can be provided to a solid surface 30 having RNA polymerase 20 immobilized thereon. In this embodiment, the rotation tag 40 can be bound to the target nucleic acid molecules 10 before or after the target nucleic acid molecules 10 are complexed with the immobilized RNA polymerase 20. In another example, the RNA polymerase 20 and the promoter-bound target nucleic acid molecules 10 can be combined and then deposited on the solid surface 30. As indicated, the rotation tag 40 can be bound to the promoter-bound target nucleic acid molecules 10 before or after the complex is deposited on the solid surface 30. In another example, rotation tags 40 can be attached to the promoter-bound target nucleic acid molecules 10 and contacted with RNA polymerase 20. The RNA polymerase 20 can be immobilized on a solid substrate 30 before introducing the rotation tagged-target nucleic acid molecules 10, or the entire complex can be deposited and immobilized on a solid substrate 30.

Figure 3A:
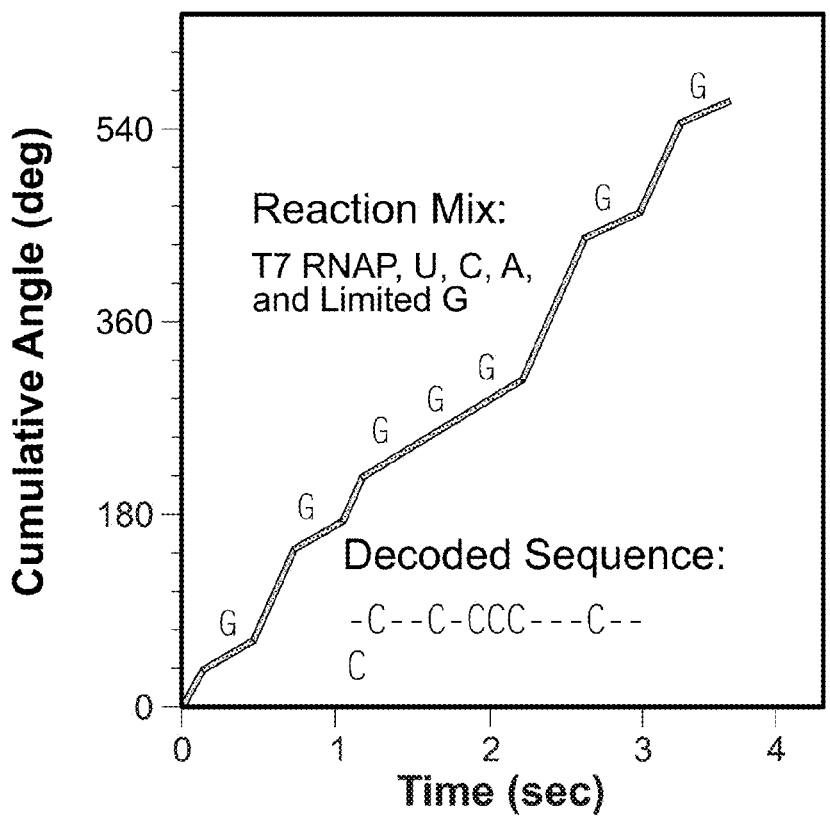
FIG. 3 are graphs showing two modes of nucleic acid sequencing described herein: Panel A shows an asynchronous, real-time "nucleotide pattern" sequencing strategy, where a limited concentration of a single nucleoside triphosphate (guanine (G) in this Panel) causes the polymerase to pause when incorporating G nucleotides into the nascent strand. Panel B shows a synchronous sequencing strategy, where a "base-by-base" introduction of nucleoside triphosphates results in a continuous decoding of the nucleotide sequence. The hypothetical transcription product (SEQ ID NO:5) is shown along the slope of the line and the corresponding DNA sequence (SEQ ID NO:6) of the hypothetical transcription product is shown at the bottom of the graph.
Figure 3B:
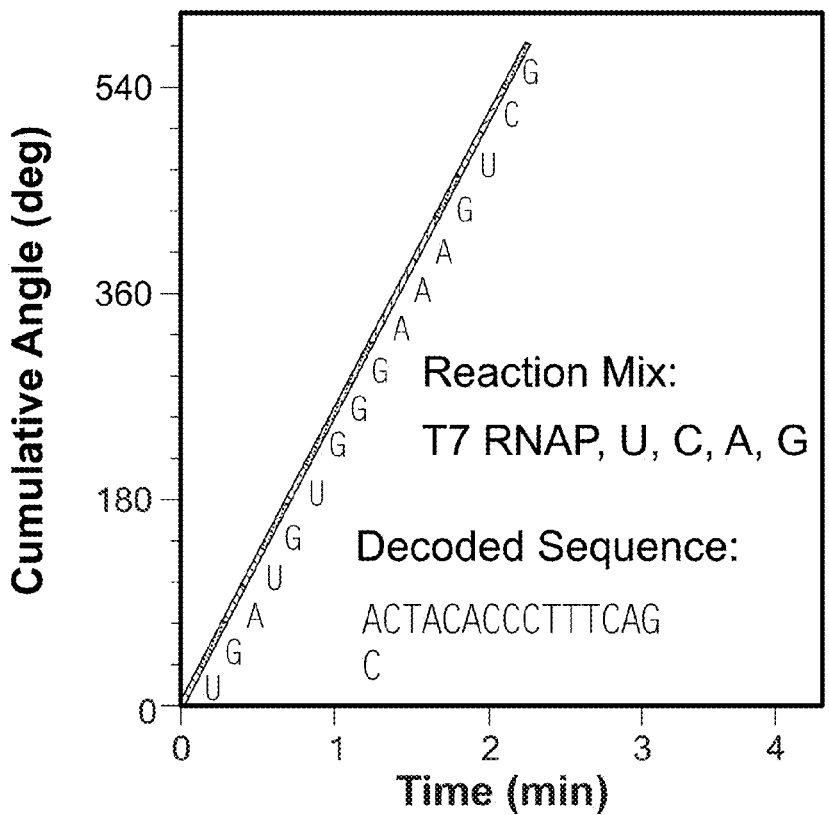

The rotation-dependent transcriptional sequencing described herein can be performed in an asynchronous (i.e., rate-limiting) mode (FIG. 3A) or a synchronous (i.e., base-by-base) mode, or any combination thereof to determine the sequence of a target nucleic acid molecule (FIG. 3B). At a minimum, "sequencing conditions," as used herein, refers to the presence of at least one nucleoside triphosphate, which can be used as described below to determine the sequence of a target nucleic acid molecule.

In addition to the presence of at least one nucleoside triphosphate as discussed in more detail herein, conditions under which sequencing reactions are performed are well known in the art. For example, appropriate buffer components (e.g., KCl, Tris-HCl, $MgCl_2$, DTT, Tween-20, BSA) can be used to provide a suitable environment for the enzyme.

a) Asynchronous Sequencing

The rotation-dependent transcriptional sequencing method described herein can be used to sequence nucleic acids based on an asynchronous incorporation of nucleotides. For asynchronous embodiments, the sequencing conditions under which the initial reaction occurs (i.e., first sequencing conditions) include the presence of four nucleoside triphosphates, where the nucleoside triphosphates are present in different amounts, at least one of which is rate-limiting and at least one of which is not rate-limiting. For example, one of the four nucleoside triphosphates is provided in a rate-limiting amount (e.g., in an amount that is less than the amount of the other three nucleoside triphosphates). In such a reaction, the RNA polymerase will effectively pause each time it tries to incorporate the nucleoside triphosphate provided in the rate-limiting amount into the transcript, and such a pause can be observed in the rotational pattern of the rotation tag as described herein.

Figure 4A:
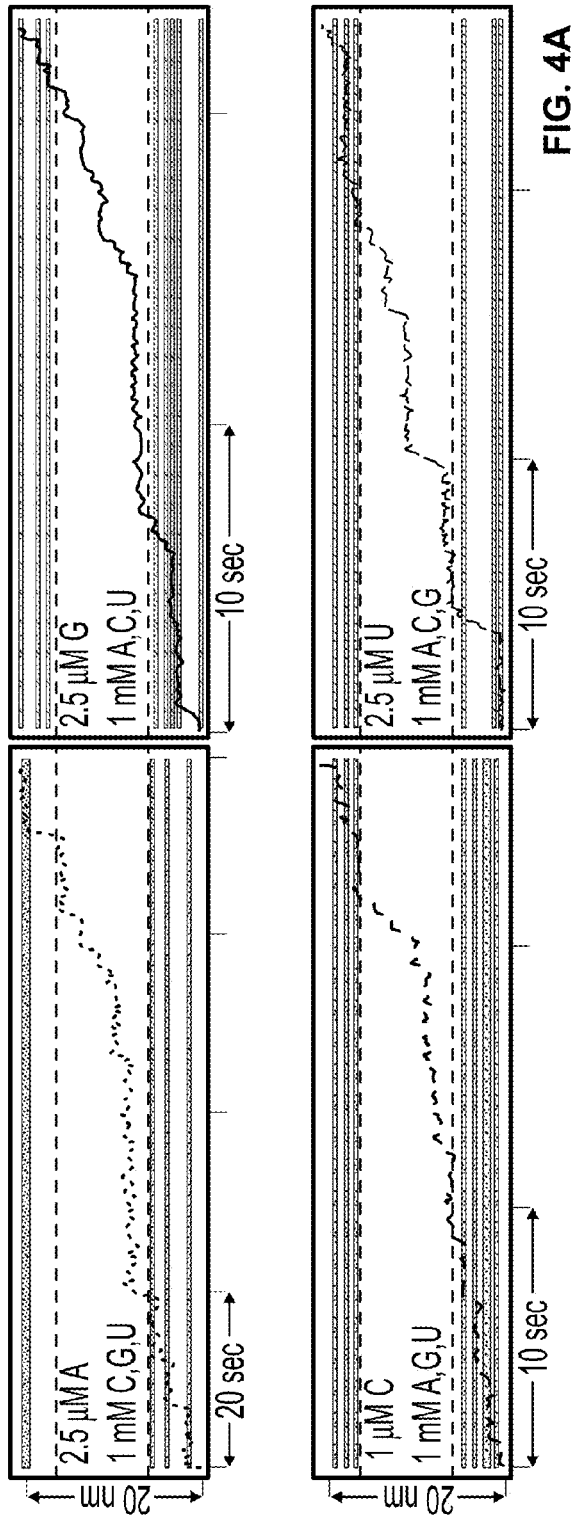
FIG. 4A are graphs from four different flow cells, each having a different nucleoside triphosphate present in a limiting amount as indicated.
Figure 4B:
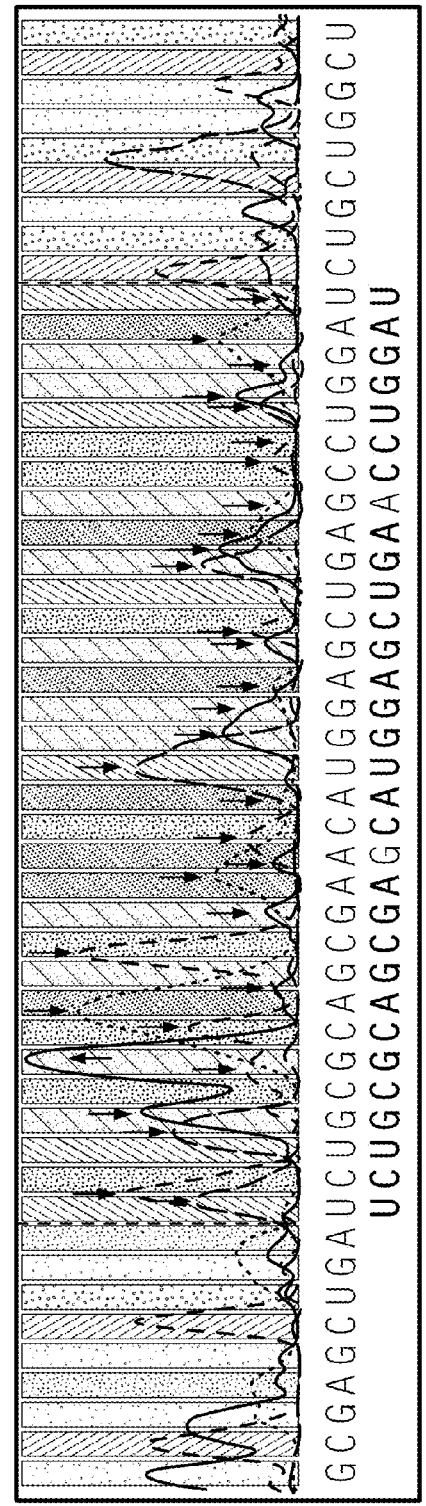
FIG. 4B shows the nucleic acid sequence of the hypothetical transcription product (SEQ ID NOs: 7 (top) and 8 (bottom)) compiled from the four flow cells.

Significantly, the number of bases between each pause can be precisely determined by detecting the cumulative amount of rotation between pauses. Thus, the precise position of, for example, each guanine (G) nucleotide along the sequence of the target nucleic acid molecule can be concisely determined due to changes in the rotational pattern when the G nucleoside triphosphate is provided in rate-limiting amounts. Similar reactions can be performed under second, third and, if desired, fourth, sequencing conditions in which, respectively, the second, third, and fourth nucleoside triphosphate of the four nucleoside triphosphates is present in a rate-limiting amount. As shown in FIG. 4, the combined information from the four reactions, whether they are performed simultaneously with one another or sequentially following one another, provide the complete sequence of the target nucleic acid molecule.

The pattern, even from a single reaction resulting in the positional sequence of one of four nucleotides can be compared to nucleic acid databases and used to identify the nucleic acid molecule with a high level of confidence. In addition, it would be understood by those skilled in the art that the sequence of a target nucleic acid molecule could be compiled using the positional information produced from three of the four nucleoside triphosphates, as the positional information of the fourth nucleotide in the sequence can be inferred once the other three nucleotides are known.

b) Synchronous or Base-by-Base Sequencing

The rotation-dependent transcriptional sequencing method described herein can be used to sequence nucleic acids in a synchronous pattern, which otherwise might be known as base-by-base sequencing. For synchronous or base-by-base embodiments, the sequencing conditions under which the initial reaction occurs (i.e., first sequencing conditions) include the presence of a single nucleoside triphosphate. In such a reaction, transcription by the RNA polymerase will only proceed if the target nucleic acid contains the complementary base at that position, which can be observed as a change in the rotational pattern of the rotation tag as described herein. Based on the structural characteristics of the double-helix, incorporation of one nucleotide by RNA polymerase results in about a 36 rotation. Such reaction conditions are continued until the rotational pattern of the rotation tag does not change. It would be understood that the cumulative change in the rotational pattern can be used to precisely determine the number of times the first nucleoside triphosphate was sequentially incorporated into the transcript (e.g., in a homopolymeric region of the target nucleic acid molecule).

When a change is no longer observed in the rotational pattern of the rotation tag under the first sequencing conditions (i.e., the presence of a first nucleoside triphosphate of the four nucleoside triphosphates), or if no changes in the rotational pattern are observed under the first sequencing conditions, a reaction is performed under second sequencing conditions. Second sequencing conditions include the presence of a second nucleoside triphosphate of the four nucleoside triphosphates. Changes in the rotational pattern of the rotation tag are indicative of transcription (i.e., the incorporation of one or more of the particular nucleoside triphosphate present into the transcript by the RNA polymerase), while the absence of a change in the rotational pattern of the rotation tag indicates that no transcription took place.

Such reactions, under first sequencing conditions, second sequencing conditions, third sequencing conditions (i.e., the presence of a third nucleoside triphosphate of the four nucleoside triphosphates) or fourth sequencing conditions (i.e., the presence of a fourth nucleoside triphosphate of the four nucleoside triphosphates), can be carried out in such a manner that the sequence of the target nucleic acid molecule is sequentially determined based on the changes in the rotational pattern and/or cumulative angle of rotation of the rotation tag under each of the respective sequencing conditions. It would be understood by those skilled in the art that steps can be taken to remove the residual nucleoside triphosphates under one sequencing condition before introducing a different sequencing condition. For example, the surface on which the RNA polymerase is immobilized can be washed or flushed before introducing a different nucleoside triphosphate. While such washing steps are not required, it would be understood that such steps would increase the accuracy of the resulting sequence information.

c) Additional Sequencing Methodologies

The rotation-dependent transcriptional sequencing methods described herein are amenable to a number of different variations and routine modifications, which can be utilized, for example, and without limitation, to increase the accuracy of the sequencing information and increase the amount of information obtained in a sequencing reaction.

For example, many RNA polymerases possess a "strand-switching" or "turn-around transcription" ability. This feature can be advantageously used in the methods described herein to increase the accuracy of the resulting sequence information. For example, when RNA polymerase reaches the end of a target nucleic acid, the RNA polymerase can "jump" to the opposite strand and continue transcription. See, for example, McAllister at al. (US 2007/0077575) and Rong et al. (1998, "Template Strand Switching by T7 RNA Polymerase", *J. Biol. Chem.*, 273(17):10253-60). In addition, certain RNA polymerases can "jump" from the double-stranded DNA template to the hybrid DNA-RNA transcript and resume transcription of the DNA strand. In addition, this type of recursive sequencing of a target nucleic acid molecule can be genetically engineered by introducing (e.g., ligating) a RNA polymerase promoter onto each end of the target nucleic acid molecule, such that the RNA polymerase binds and transcribes the opposite strand.

In addition, one or more different RNA polymerases (e.g., RNA polymerases from different organisms or different RNA polymerases from the same organism) can be immobilized onto a solid surface. As is known in the art, different RNA polymerases recognize and bind to different promoter sequences. Therefore, one or more different RNA polymerase promoters can be ligated to different populations of target nucleic acid molecules and a combined population of target nucleic acid molecules can be sequenced, based on the rotational pattern of the rotation tag, using the one or more different RNA polymerases immobilized on the solid surface. By differentially-labeling, for example, the different RNA polymerases or the different populations of target nucleic acid molecules (using, for example, beads emitting different wavelengths, fluorescent tags, or fluorescently-labeled antibodies), the sequence of one population of target nucleic acid molecules can be distinguished from the sequence of another population of target nucleic acid molecules. Using such methods, sequencing reactions on different populations of target nucleic acid molecules can take place simultaneously.

In some embodiments, both the RNA polymerases and the populations of target nucleic acid molecules can be differentially labeled. It would be understood that labeling the target nucleic acid molecules can occur directly via the nucleic acid or, for example, via the rotation tag. This ability to differentially label at multiple levels of the sequencing reaction can be used, for example, to compare the processivity of different RNA polymerases on target nucleic acid molecule having the same sequence, which may identify, for example, homopolymeric regions or regions of methylation, or to compare the transcription of target nucleic acid molecules having different sequences by more than one RNA polymerase.

Simply by way of example, any combination of RNA polymerase enzymes (e.g., from one or more of the T7, T3, SP6 or K11 bacteriophages), in conjunction with the appropriate nucleic acid promoter sequences, can be used in the rotation-dependent transcriptional sequencing methods described herein. As discussed herein, this feature allows for a multiplexing of the sequencing reactions. Other variations that utilize different RNA polymerases in conjunction with their specific promoter sequences as well as differential-labeling techniques are contemplated herein.

In some embodiments, two asynchronous rotation-dependent transcriptional sequencing reactions can be performed under the same sequencing conditions (e.g., first sequencing conditions). Once sequencing has progressed for a sufficient number of nucleotides (e.g., at least 100 nt, 500 nt, 1,000 nt, 5,000 nt, or 10,000 nt), the sequencing conditions of one of the reactions can be changed (e.g., to second sequencing conditions), and the rotation-dependent transcriptional sequencing continued. The resulting sequence information obtained under the first sequencing conditions can be used to align a particular target nucleic acid molecule in the first reaction with the same particular target nucleic acid, molecule in the second reaction, which, when the sequencing conditions are changed, allows positional sequence information to be obtained for two nucleotides within a particular target nucleic acid molecule.

Those skilled in the art would understand that, due to the torsion place on the nucleic acid molecules by the RNA polymerase, the rotation tag may produce a "load", possibly slowing down the RNA polymerase. This can be prevented or diminished, for example, by using a rotation tag having a different shape (e.g., two oblong beads or a bead-rod combination), which can result in more friction in the fluidic medium than a simple spherical bead. On the other hand, there may be RNA polymerases and/or sequencing conditions in which a mechanical loading of the RNA polymerase can be used to advantageously affect the rate of sequencing.

Articles of Manufacture/Kits

Articles of manufacture (e.g., kits) are provided herein. An article of manufacture can include a solid substrate, as discussed herein, onto which a plurality of RNA polymerase enzymes is immobilized. A plurality of RNA polymerase enzymes refers to at least 10 RNA polymerases (e.g., at least 20, 50, 75, or 100 enzymes), at least 100 RNA polymerases (e.g., at least 200, 500, or 1,000 enzymes), or at least 1,000 RNA polymerases (e.g., at least about 2,500, 5,000, 10,000, or 50,000 enzymes).

Articles of manufacture are well known in the art and can include packaging material (e.g., blister packs, bottles, tubes, vials, or containers) and, in addition to the solid surface having RNA polymerases immobilized thereon, can include one or more additional components.

In some embodiments, an article of manufacture can include a rotation tag. As described herein, the rotation tag can be a non-spherical tag or a spherical tag having a non-uniform feature that can be used to detect rotation.

In some embodiments, an article of manufacture can include nucleic acid sequences corresponding to a RNA polymerase promoter. As discussed herein, promoters that direct transcription by RNA polymerases are well known and used routinely in the art.

In some embodiments, an article of manufacture can include a tether. As discussed herein, a tether can be used to attach target nucleic acid molecules to rotation tags. In some embodiments, a tether includes nucleic acid sequences, which, for example, can be biotinylated, such that they bind to streptavidin-labeled beads.

In some embodiments, an article of manufacture can include one or more nucleoside triphosphates. When more than one nucleoside triphosphate is provided, they can be provided in combination (e.g., in a single container) or separately (e.g., in separate containers).

In some embodiments, an article of manufacture further includes instructions. The instructions can be provided in paper form or in any number of electronic forms (e.g., an electronic file on, for example, a CD or a flash drive, or directions to a site on the internet (e.g., a link). Such instructions can be used to identify rotation of the rotational tag relative to an axis through the magnetic reference tag, compile the sequence of a target nucleic acid molecule based on the rotational pattern and the presence of a nucleoside triphosphate; and/or apply an appropriate tension on the nucleic acid.

Rotation-Dependent Transcriptional Sequencing Systems

A rotation-dependent transcriptional sequencing system as described herein includes at least a Sequencing Module. A Sequencing Module for sequencing target nucleic acid molecules typically includes a receptacle for receiving a solid substrate, a tension source for providing directional force, a light source for projecting light onto a rotation tag, and optics for detecting the pattern of rotation of the rotation tag. The tension source, light source, and optics are discussed herein. A receptacle for receiving a solid substrate can be configured, for example, as a recessed chamber. Generally, a solid substrate for use in a rotation-dependent transcriptional sequencing system will have a plurality of RNA polymerases immobilized thereon, and, for a high throughput sequencing system, the solid surface can be an on-chip embodiment as described herein. A Sequencing Module also can include a computer processor or means to interface with a computer processor. Further, primary analysis software can be provided as part of a Sequencing Module.

In addition, a Sequencing Module further can include a heating and cooling element and a temperature control system for changing and regulating the temperature of the sequencing reactions. In addition, a Sequencing Module further can include fluidics (e.g., one or more reagent or buffer reservoirs and tubing for delivering the one or more reagents or buffers to the reaction chamber (e.g., the chip)). Fluidics for delivering one or more reagents or buffers also can include, without limitation, at least one pump. Without limitation, exemplary reagents that can be used in a sequencing reaction can include, for example, nucleoside triphosphates, enzymes (RNA polymerase) and rotation tags. Also without limitation, exemplary buffers that can be used in a sequencing reaction can include, for example, of a wash buffer, an enzyme-binding buffer and a sequencing buffer.

Figure 5:
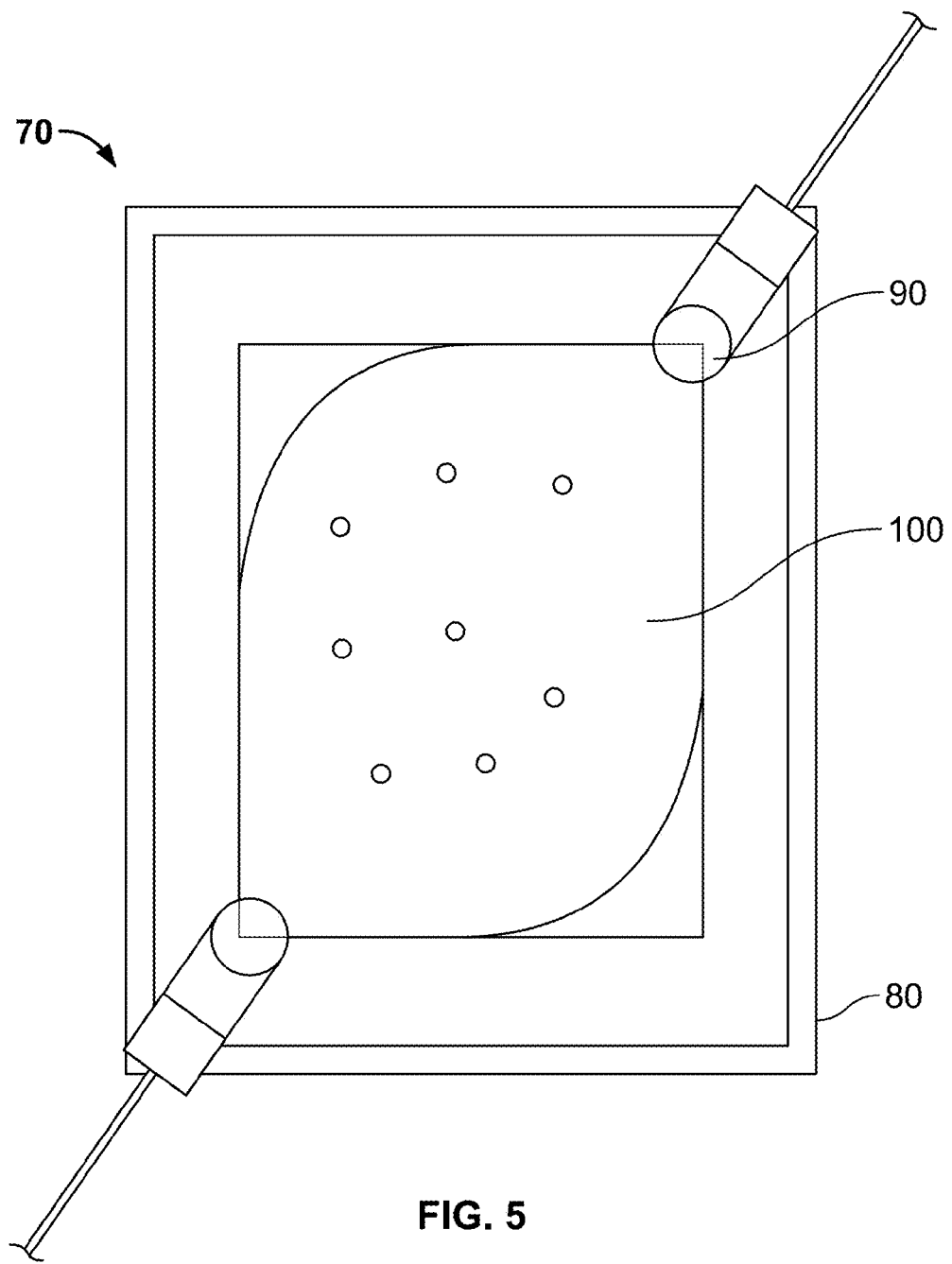
FIG. 5 is a schematic showing one embodiment of a flow cell as described herein. For example, a flow cells can include a laser-cut Pressure Sensitive Adhesive (PSA) film of approximately 50 micron thickness laid on top of an Omni Vision sensor (OV14810; after removal of the window and coating with SiN). This configuration results in a flow cell on top of a CMOS chip. A glass or polymeric slide, having holes for microfluidic feed-through tubes, is then applied.
Figure 6A:
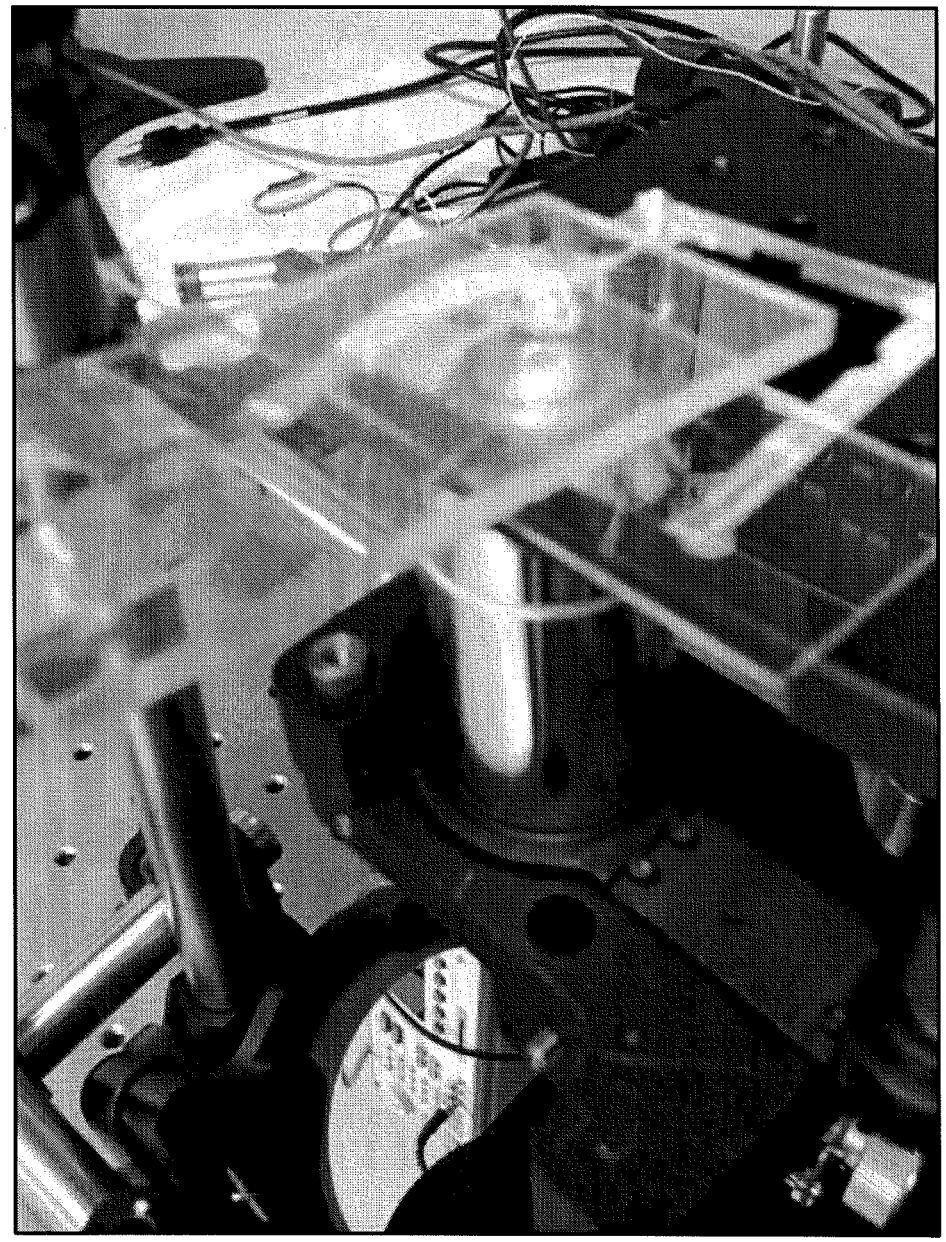
FIG. 6A is a photograph and FIG. 6B is a line drawing showing a prototypical solid surface in which fibers are used to deliver light and a microscope objective is used for imaging. A solid surface slide containing rotation-tagged nucleic acids and RNA polymerases is shown positioned below the fibers and above the objective.
Figure 6B:
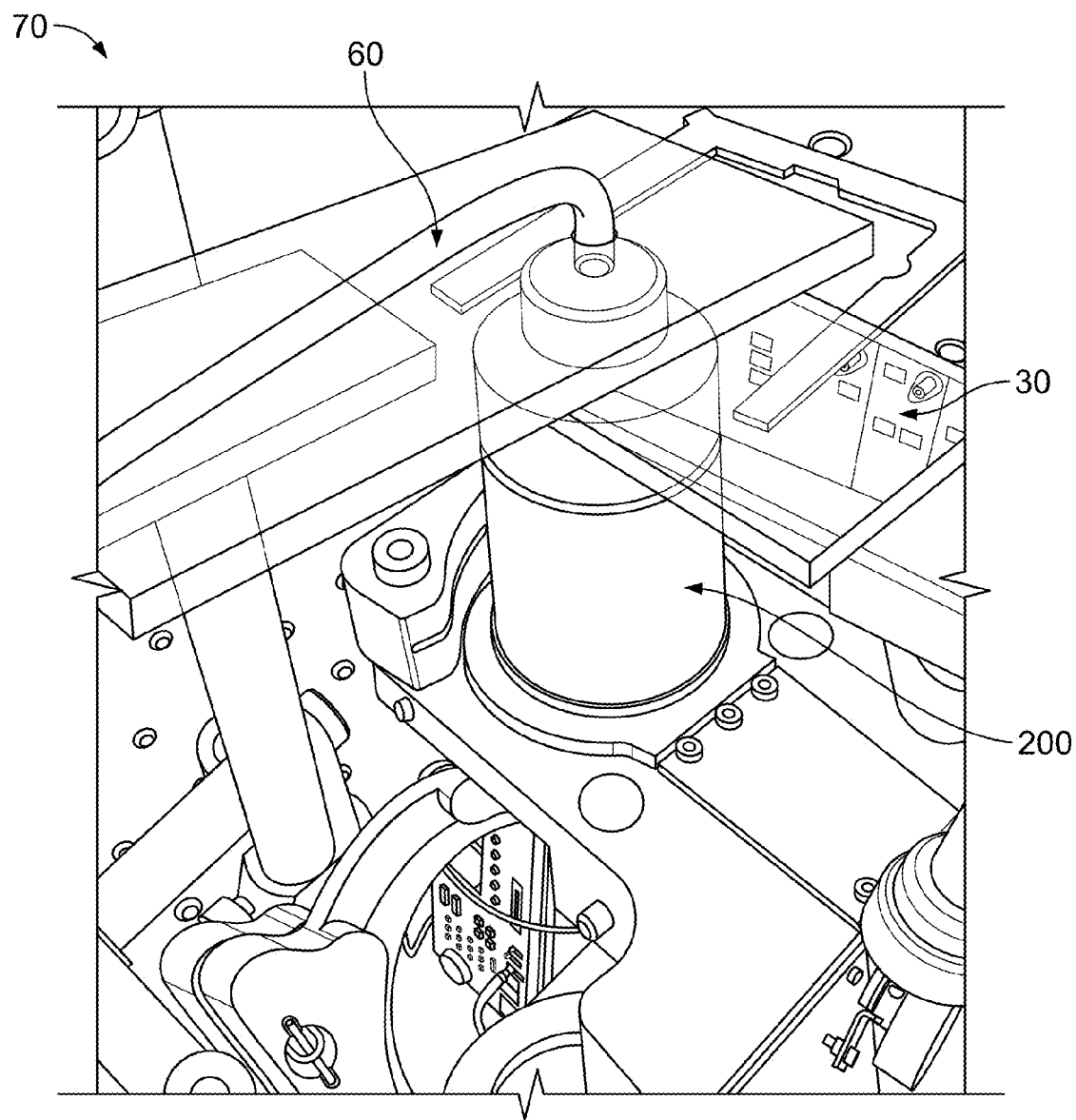

FIG. 5 is a schematic showing a representative flow cell 70. In the flow cell 70 shown, a laser-cut Pressure Sensitive Adhesive (PSA) film approximately 50 microns thick is laid on top of an OmniVision sensor (OV14810; after removal and coating of the window with SiN). This configuration results in a flow cell on top of a CMOS chip 80. A glass or polymeric slide, having holes for microfluidic feed-through tubes 90, is then applied. Multiple rotation-dependent transcriptional complexes 100 are shown in the field. FIG. 6 shows a photograph (Panel A) and a line drawing (Panel B) of a representative flow cell 70 in which fibers 60 are used to deliver light and a microscope objective 200 is used for imaging. The solid surface 30 also is shown.

Figure 7:
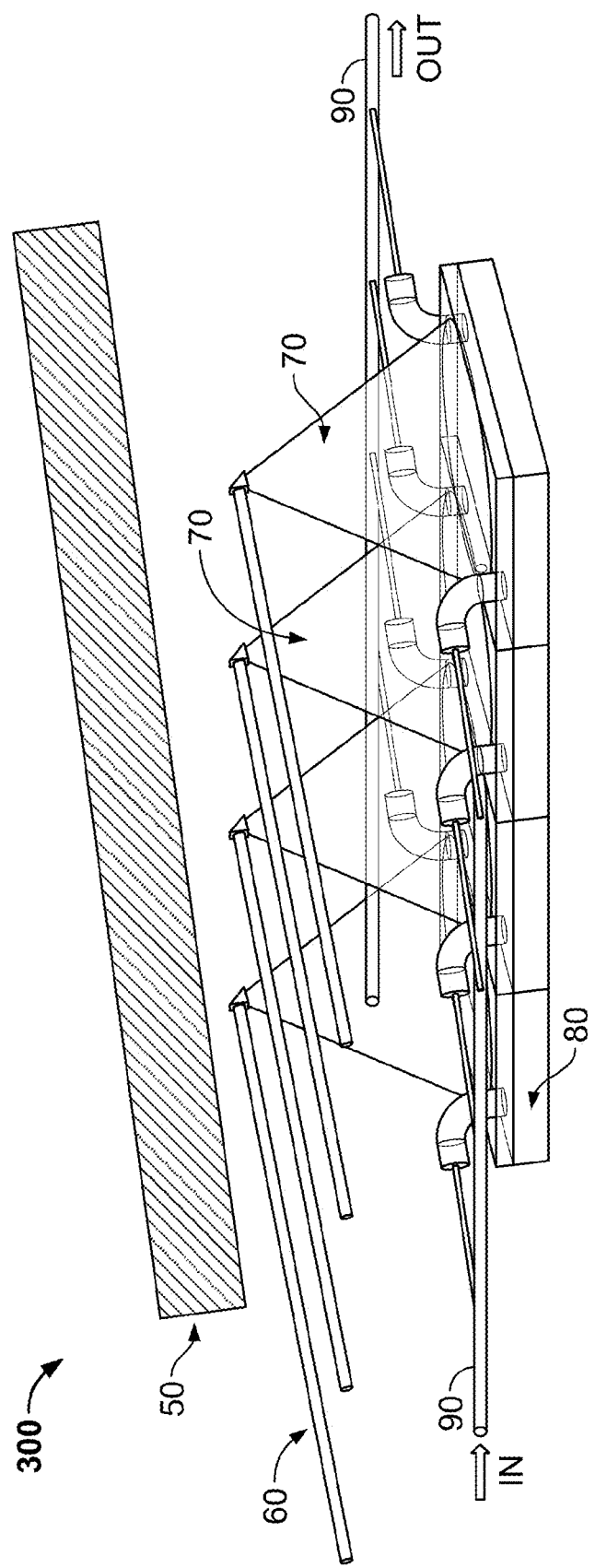
FIG. 7 shows one embodiment of a rotation-dependent transcriptional sequencing system as described herein. The schematic shows a tension source, a source of illumination, and four flow cells on top of solid surface chips with in- and out-fluidics.

FIG. 7 is a schematic showing a rotation-dependent transcriptional sequencing system 300. The schematic shows the tension source 50, the light sources 60, and the flow cells 70 with in- and out-fluidics 90. The flow cells 70 in FIG. 7 are shown on a chip 80 (e.g., CMOS, CCD, or modified versions thereof).

Figure 8A:
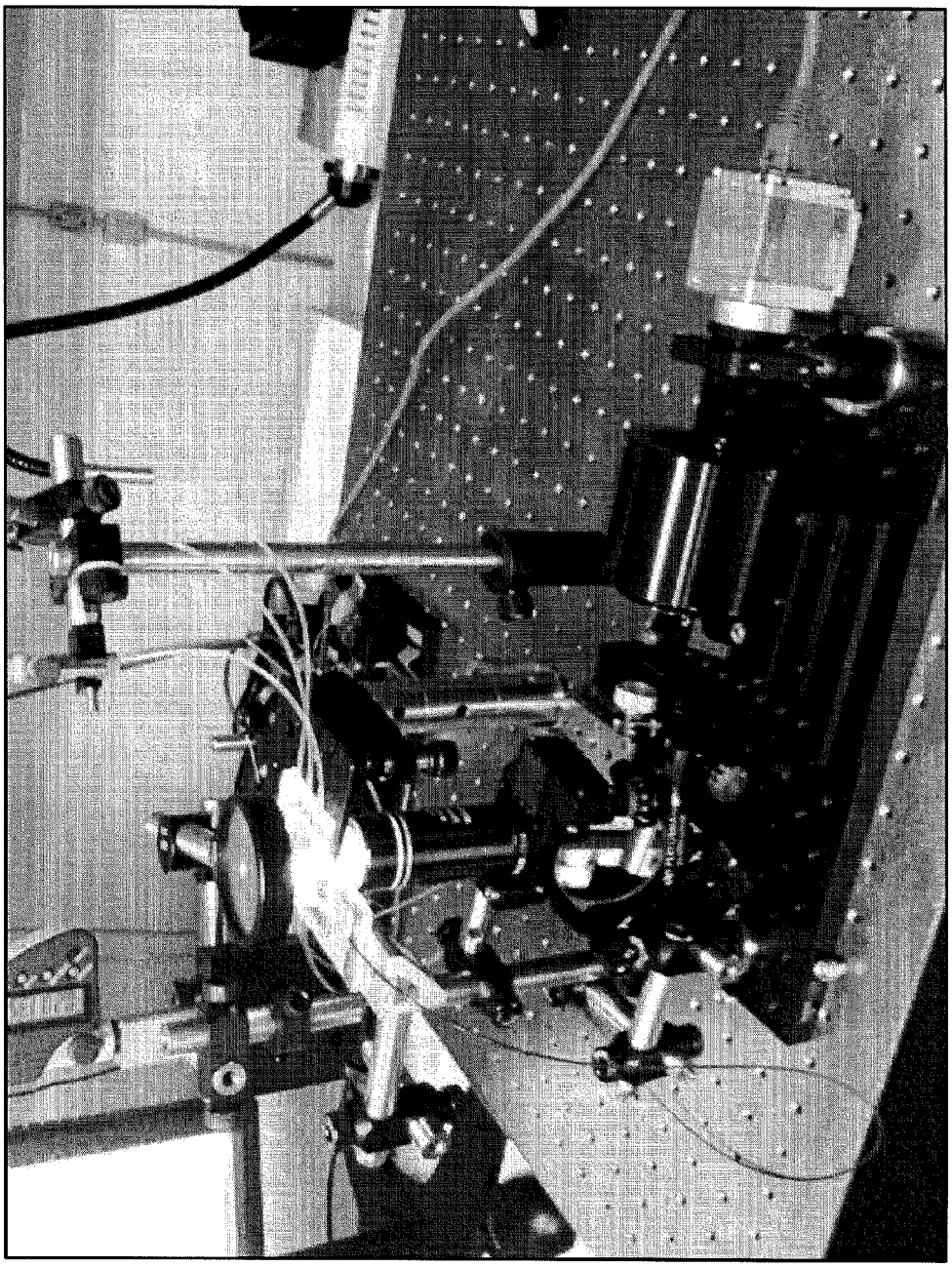
FIG. 8A is a photograph and FIG. 8B is a line drawing showing one embodiment of a rotation-dependent transcriptional sequencing system. This embodiment uses a 20× water-objective, "super-lens" from Olympus that provides more than 1 mm FOV with NA=0.9, which is high resolution with a large field of view. The solid surface, light delivery and tension source (e.g., a magnet) are also shown.
Figure 8B:
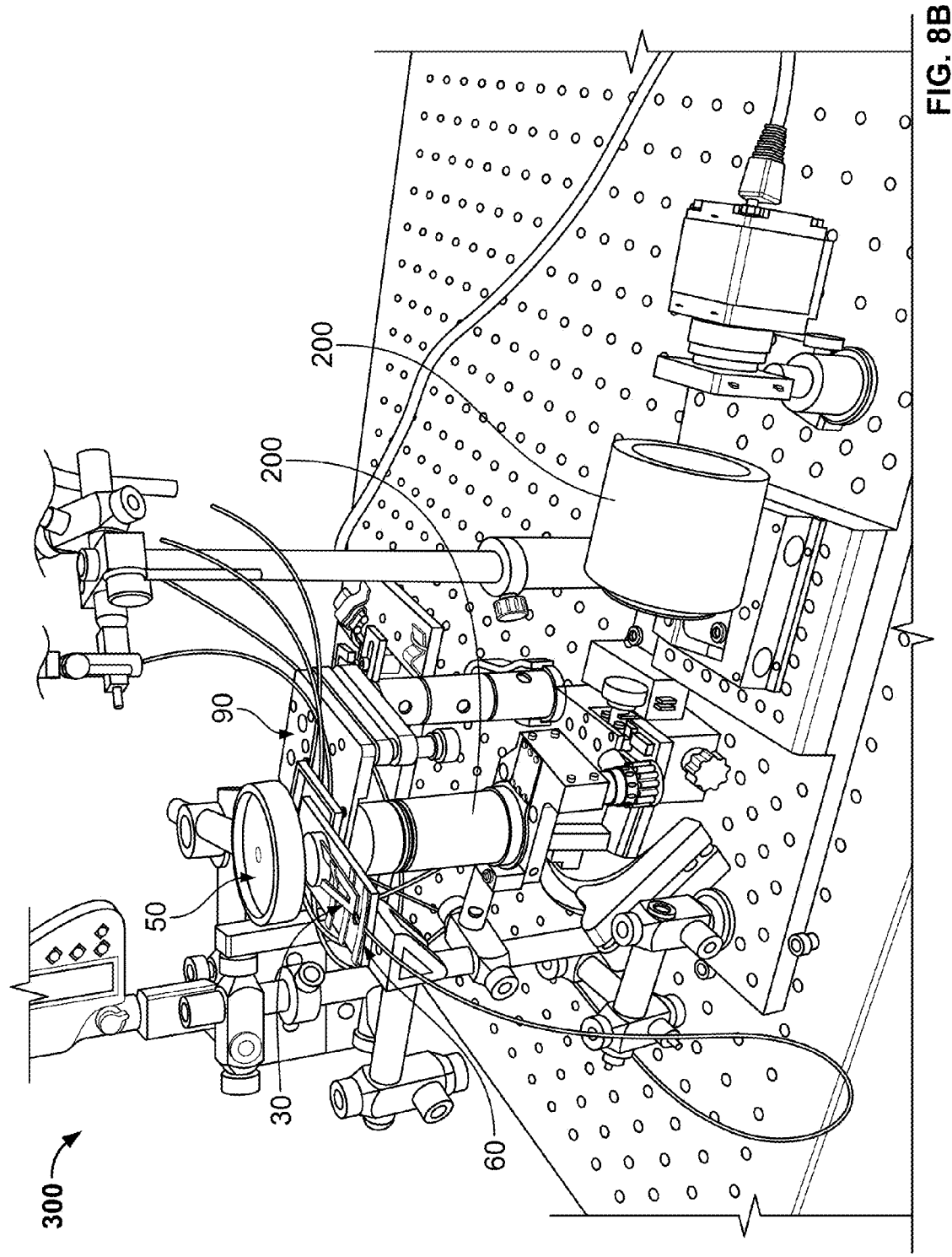
Figure 9A:
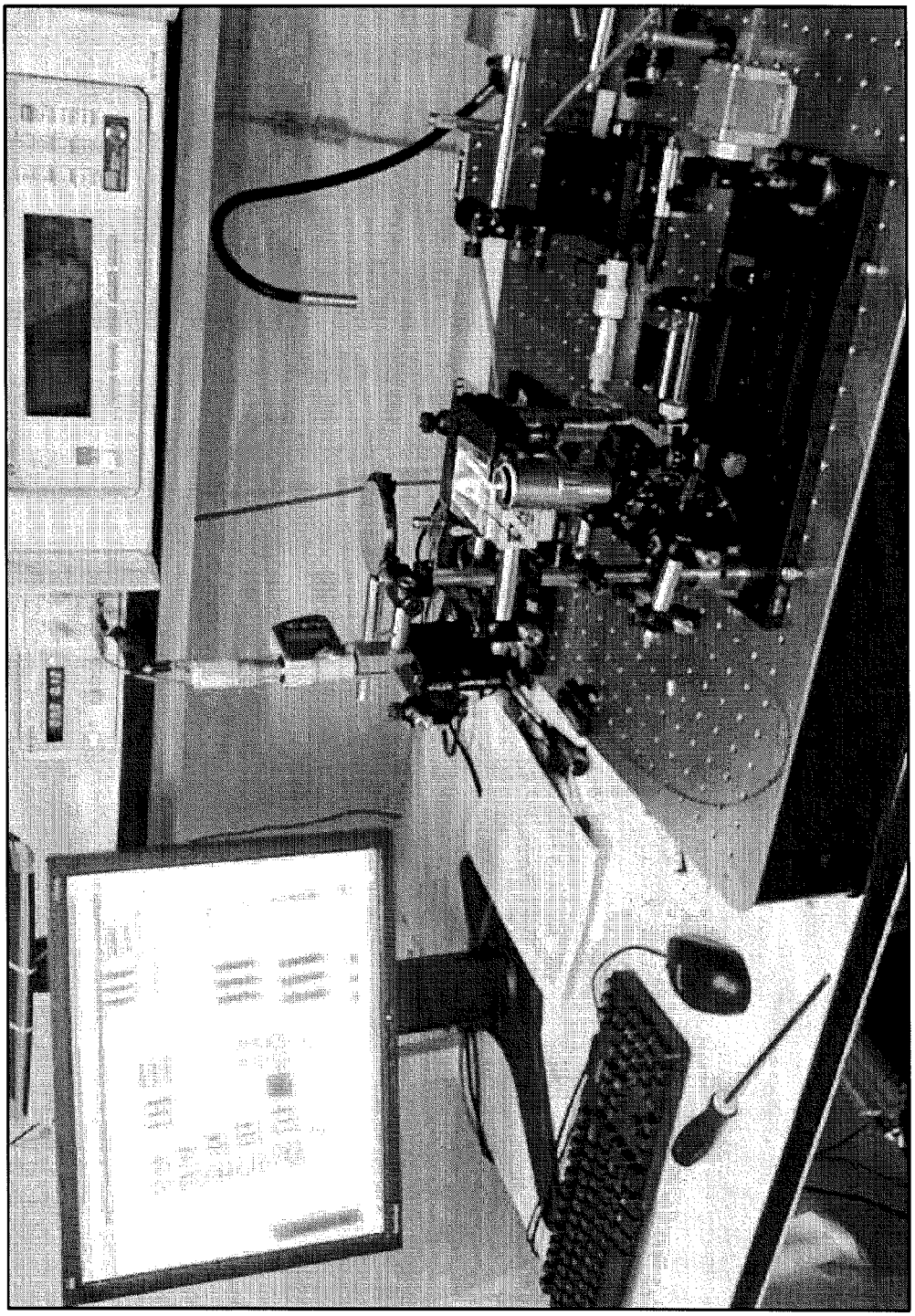
FIG. 9A is a photograph and FIG. 9B is a line drawing showing another embodiment of a rotation-dependent transcriptional sequencing system. In this embodiment, a compact optical system is shown with an AF optical resolution target, illumination fibers, a 20× Mitutoyo objective, tube lens and camera. A disk magnet is also visible above the target but out of the way for this image. For 1 micron resolution at objective space, one or more cameras having a pixel size greater than 20 micron can be used.
Figure 9B:
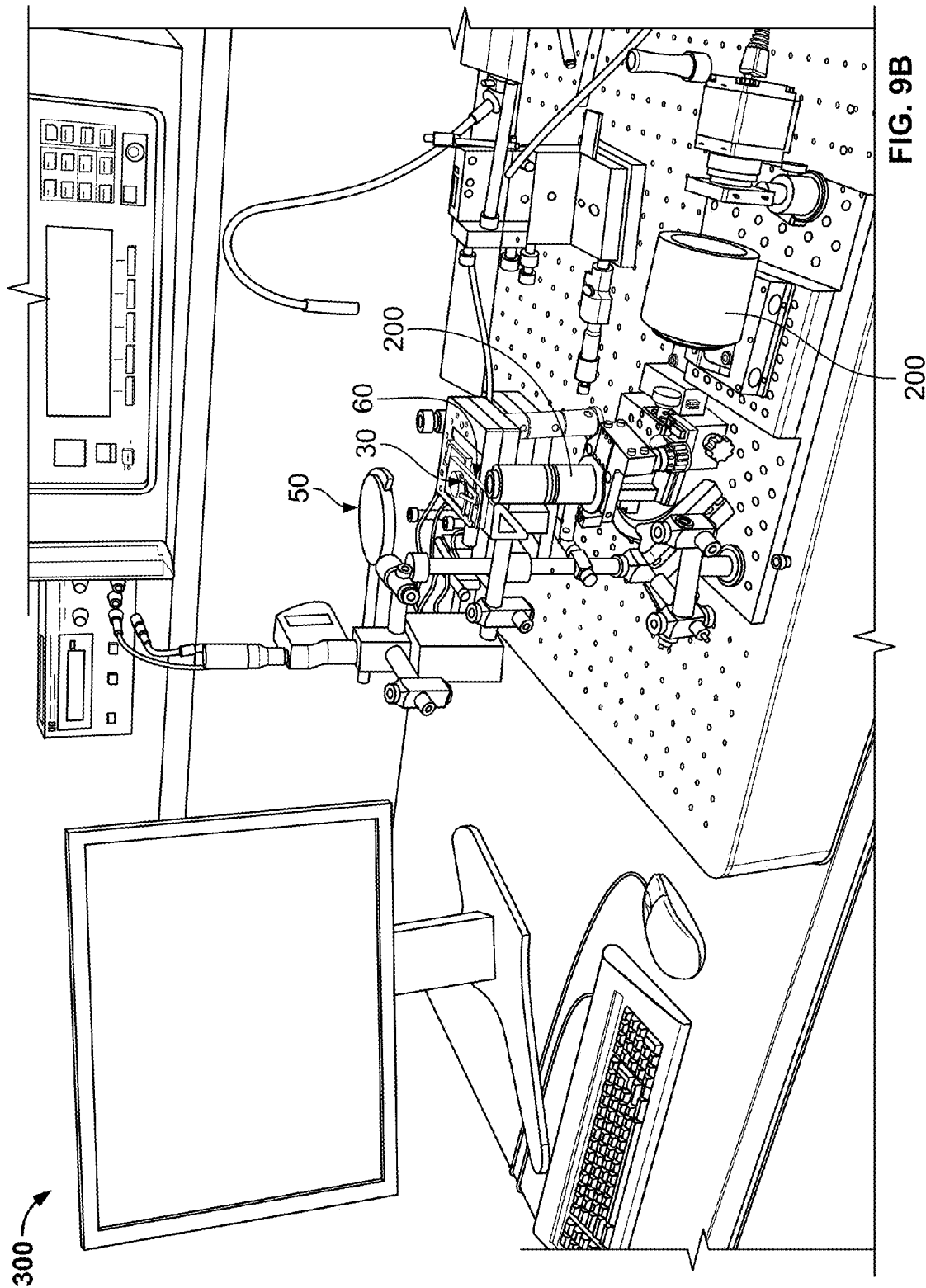

FIGS. 8A and 9A show photographs of different embodiments of a rotation-dependent transcriptional sequencing system 300 as described herein, and FIGS. 8B and 9B are the respective line drawings of the embodiments shown in each photograph. Referring to FIGS. 8B and 9B, both of the rotation-dependent transcriptional sequencing systems 300 show a solid surface 30, a light source 60, and fluidics 90 for delivering and removing the various reagents and/or buffers. A tension source 50 is shown in each of FIGS. 8 and 9; in FIG. 9, the tension source 50 is moved out of the way to more easily access the flow cell on the solid surface 30. The rotation-dependent transcriptional sequencing systems 300 in FIGS. 8 and 9 both utilize similar optics 200. The system 300 in FIG. 8 utilizes a 20× water-objective 200 (here, a "super-lens" from Olympus, which provides more than 1 mm FOV with NA=0.9, i.e. high resolution with a large field of view), and the system 300 in FIG. 9 utilizes a 20× objective tube lens 200. Both FIGS. 8 and 9 also include a camera 200.

In one embodiment, structured illumination and stroboscopy can be used in a rotation-dependent transcriptional sequencing system as follows. For example, two or more fibers each can be coupled to a separate LED and their illumination directed in different angles with respect to the plane of the solid surface. The light sources can be independently controlled in light intensity (or "amplitude"), in spectral content (e.g. different color LEDs or filtered white LEDs) and in time (e.g. via triggering the electronics from a single trigger but after different delays incorporated in the timing of the trigger). The same trigger, but, for example, at a different delay or amplitude or shape, can initiate the exposure of the camera. Since the exposure duration of the camera can be controlled separately, it is feasible to time the first light source (e.g., reflection can be captured, for example, by the even number frames) and the second light source (e.g., reflection can be captured, for example, by the odd number frames) to illuminate the rotation tag and its signature. Since the illumination is at different angles (e.g. one from the top and one from the bottom, i.e., in an epiposition, or one from top and one at, e.g., a 45° angle to the vertical), the rotation tag can be detected in one image and not in the another image. Since a series of images is captured, and since more than one source can be used, it is possible to reconstruct virtually a three-dimensional shape of the rotation tag in every frame. This level of detection leads to higher accuracy and fewer deletion errors in the final sequence.

The rotation-dependent transcriptional sequencing systems described herein can significantly advance point-of-care diagnostics and genomics based on massively parallel single molecule analysis with the single nucleotide resolution. The system is intrinsically suited for highly multiplexed target identification and has unlimited flexibility in being able to be reconfigured to interrogate simultaneously or sequentially different nucleic acid targets, e.g. pathogens and human biomarkers. In addition, while current PCR- and microarray-based methods of sequencing nucleic acids are limited by being able to detect only known sequences or infectious agent(s) because of the specific set of reagents (primers and probes) required for positive identification.

For a system designed, for example, for high-throughput clinical diagnostics or for point-of care diagnostics, a rotation-dependent transcriptional sequencing system as described herein can be coupled with a Sample Preparation Module and a Template Finishing Module.

A Sample Preparation Module can be configured to lyse cells, thereby releasing the nucleic acids, and a Sample Preparation Module also can have the capability of shearing/fragmenting the nucleic acid. A Sample Preparation Module typically includes a receptacle for receiving a biological sample, and fluidics for delivering one or more reagents or buffers to the biological sample. A Sample Preparation Module can be configured to receive a variety of different biological samples or a Sample Preparation Module can be configured to receive a specific type of biological sample (e.g., a swab, a tissue sample, a blood or plasma sample, saliva, or a portion of a culture) or a biological sample provided in a specific form (e.g., in a vial or tube or on blotting paper). A Sequencing Preparation Module also can be configured to capture certain molecules from the biological sample (e.g., bacterial cells, viruses, etc.) using, for example, filters, columns, magnets, immunological methods, or combinations thereof (e.g., Pathogen Capture System, NanoMR Inc.).

A Sample Preparation Module can include reagents or buffers involved in obtaining the nucleic acids from a biological sample and preparing the nucleic acids for sequencing. For example, reagents involved in obtaining nucleic acids for sequencing include cell lysis reagents, nucleic acid cleavage enzymes, DNA polymerases, oligonucleotides, and/or DNA binding agents (e.g., beads or solid matrices to bind and wash the target nucleic acid molecules), while buffers involved in obtaining nucleic acids for sequencing include lysis buffer, wash buffer, elution buffer, or binding buffer. Since the rotation-dependent transcriptional sequencing described herein requires double-stranded nucleic acid templates, a Sample Preparation Module can include the necessary reagents and buffers to convert single-stranded DNA or RNA to double-stranded nucleic acid molecules (e.g., PCR reagents).

Many of the functional components of a Sample Preparation Module are commercially available (e.g. Silica gel membrane (Qiagen or Ambion kits) or as an integrated part of Palladium System (Integrated Nano Technologies Inc.)). In addition, as an alternative to enzymatic cleavage of nucleic acid templates, instruments that fragment nucleic acids are commercially available (e.g., Covaris).

A Template Finishing Module can be configured to attach RNA polymerase promoter sequences and rotation tags to target nucleic acid molecules. A Template Finishing Module typically includes fluidics for delivering one or more reagents or buffers to the target nucleic acid molecules. For example, a Template Finishing Module can include reagents and buffers for the purpose of ligating RNA polymerase promoter sequences to the target nucleic acid molecules, and a Template Finishing Module also can include reagents and buffers for attaching a rotation tag to the target nucleic acid molecules. For example, reagents involved in ligating promoter sequences or binding rotation tags to target nucleic acid molecules include, obviously, the promoter sequences and the rotation tags, but also can include, for example, ligase enzymes, a tether or PCR reagents, while buffers involved in ligating promoter sequences or binding rotation tags to target nucleic acid molecules include ligation buffer, rotation tag-binding buffer, enzyme-binding buffer, washing buffer and sequencing buffer.

Depending upon the configuration of the rotation-dependent transcriptional sequencing system as described herein, the plurality of RNA polymerases can be immobilized on the solid surface prior to introducing the promoter- and rotation tag-bound target nucleic acid molecules. Alternatively, the plurality of RNA polymerases can be combined with the promoter- and rotation tag-bound target nucleic acid molecules and the entire complex deposited on the solid surface. The latter procedure is feasible because the binding kinetics for RNA polymerases and their corresponding promoter sequences is very fast, efficient and specific.

Sequence Determination Following Rotation-Dependent Transcriptional Sequencing

Figure 10:
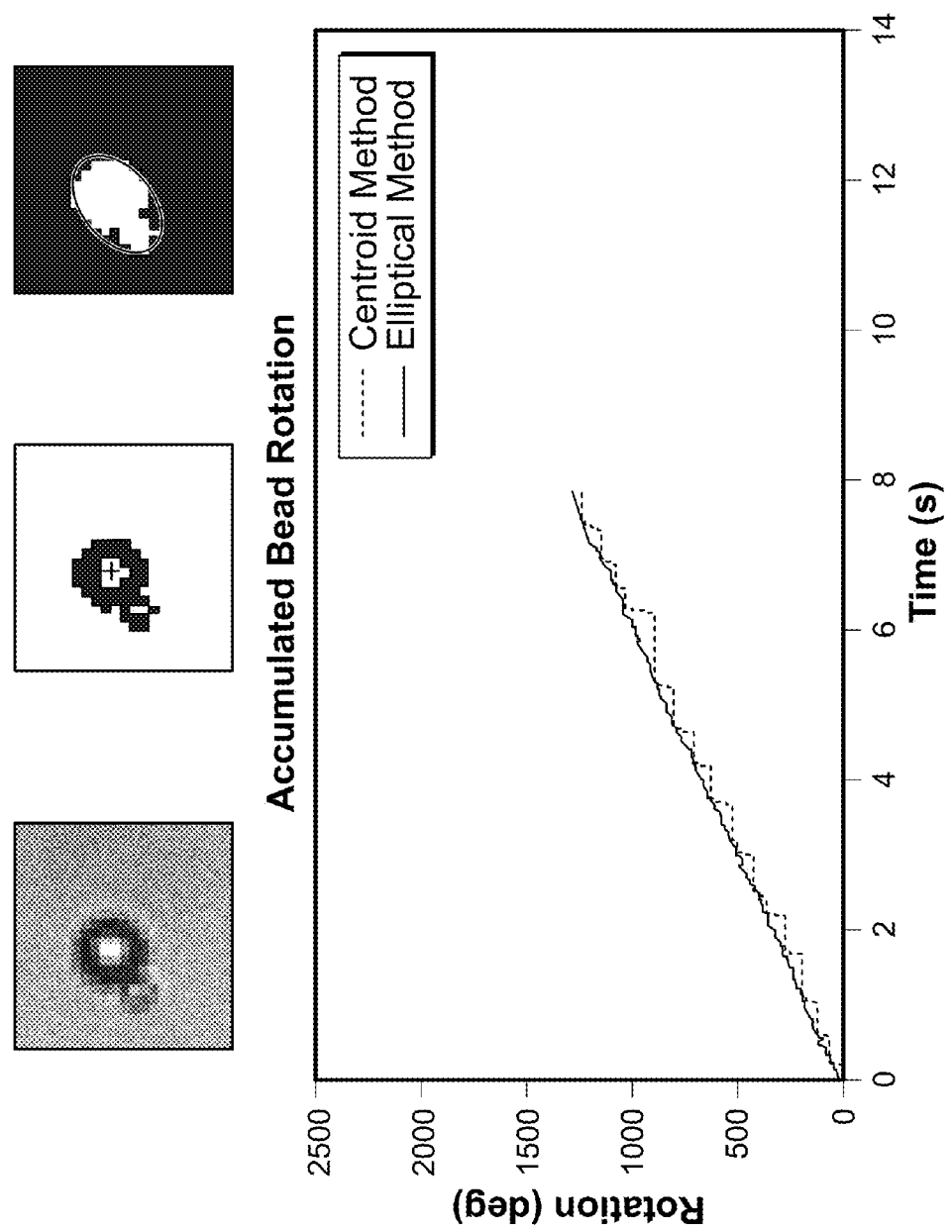
FIG. 10 shows that rotation of a rotation tag (e.g., a doublet comprising a first tag and a second tag) can be detected even when using low resolution (i.e. 10×10 pixels per bead imaged through an objective or via the on-chip method). Further reduction to 5×5 pixels is possible using more advanced algorithms. Furthermore, if a tapered bundle is used, then the resolution increases for each bead that is located on top of the bundle cores by a factor related to the size of the cores and the size of each pixel at the other side of the bundle, as well as the number of pixels on the detector the cores span.

FIG. 10 shows a screenshot of video and the corresponding digitization of the rotational pattern of a rotation tag (top), which is then shown in graphical form (bottom). The rotation tag is a 2.8 micron streptavidin-coated bead with a 1 micron biotin-coated bead attached thereto. Transcription was performed by a His-tagged RNA polymerase in the presence of all four nucleoside triphosphates. FIG. 10 demonstrates that a rotational pattern of a rotation tag can be clearly and reliably detected and measured from the images captured with a detector.

Figure 11A:
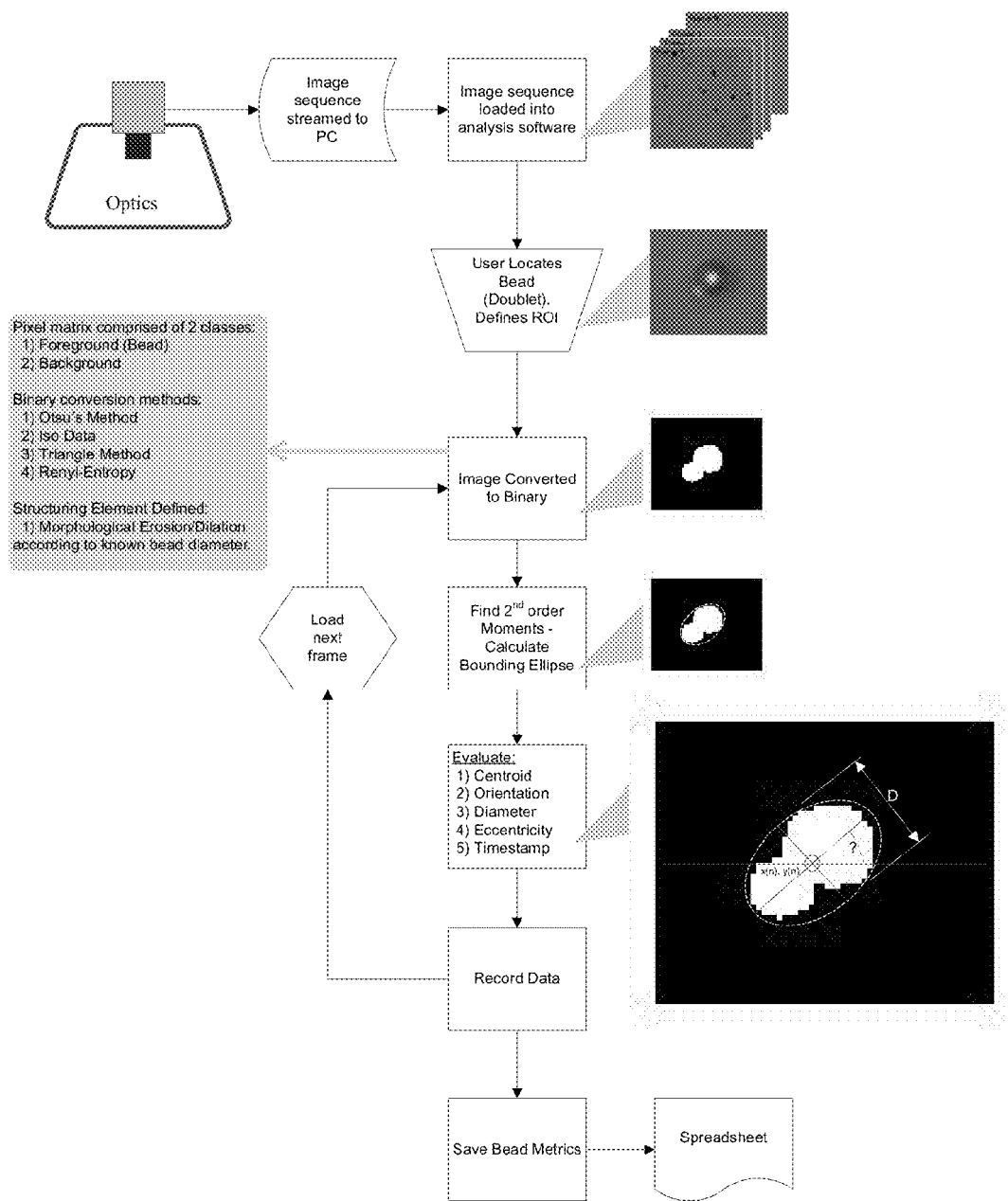
FIG. 11A is a flow diagram illustrating an example analysis of the rotational pattern of a rotation tag.

FIG. 11A is a flow diagram illustrating rotational analysis. A number of metrics can be determined from the rotational analysis, including a timestamp, displacement (from n=1 and n–1), displacement bounding circle, bead diameter, doublet orientation, accumulated rotation, angular velocity, and ellipse eccentricity. Image segmentation can be used to separate each pixel into two classes, foreground (the rotation tag) and the background. Using one method (the Otsu's method), the image histogram and the probabilities of each intensity level can be calculated, and then the threshold that minimizes intra-class variance can be determined. Using another method (Triangle method), a line is drawn between the max of the histogram at b on the gray level axis and the lowest value a on the gray level axis. The distance L normal to the line and between the line and the histogram is computed for all valudes from a to b. The level where the distance between the histogram and the line is maximal corresponds to the threshold value. Using yet another method (Adaptive mean or median), a localized window (i.e., 5×5 pixels) can be used to find the maximum intensity variance, which then is used to compute the mean or median for that window.

The bounding ellipse method can utilize any of several methods: the centroid method, which is normalized to the $2^{nd}$-order moments of the foreground (rotation tag) region; the ellipse major axis method, which, on the centroid of the region, the maximum distance to the region edge is the first point of the major axis and the reflection (from the centroid) is the $2^{nd}$ point; the ellipse minor axis method, which, on the centroid of the region, is the maximum distance to the region edge and perpendicular to the major axis; and the ellipse orientation method, which is the angle between the ellipse major axis and the x axis.

Figure 11B:
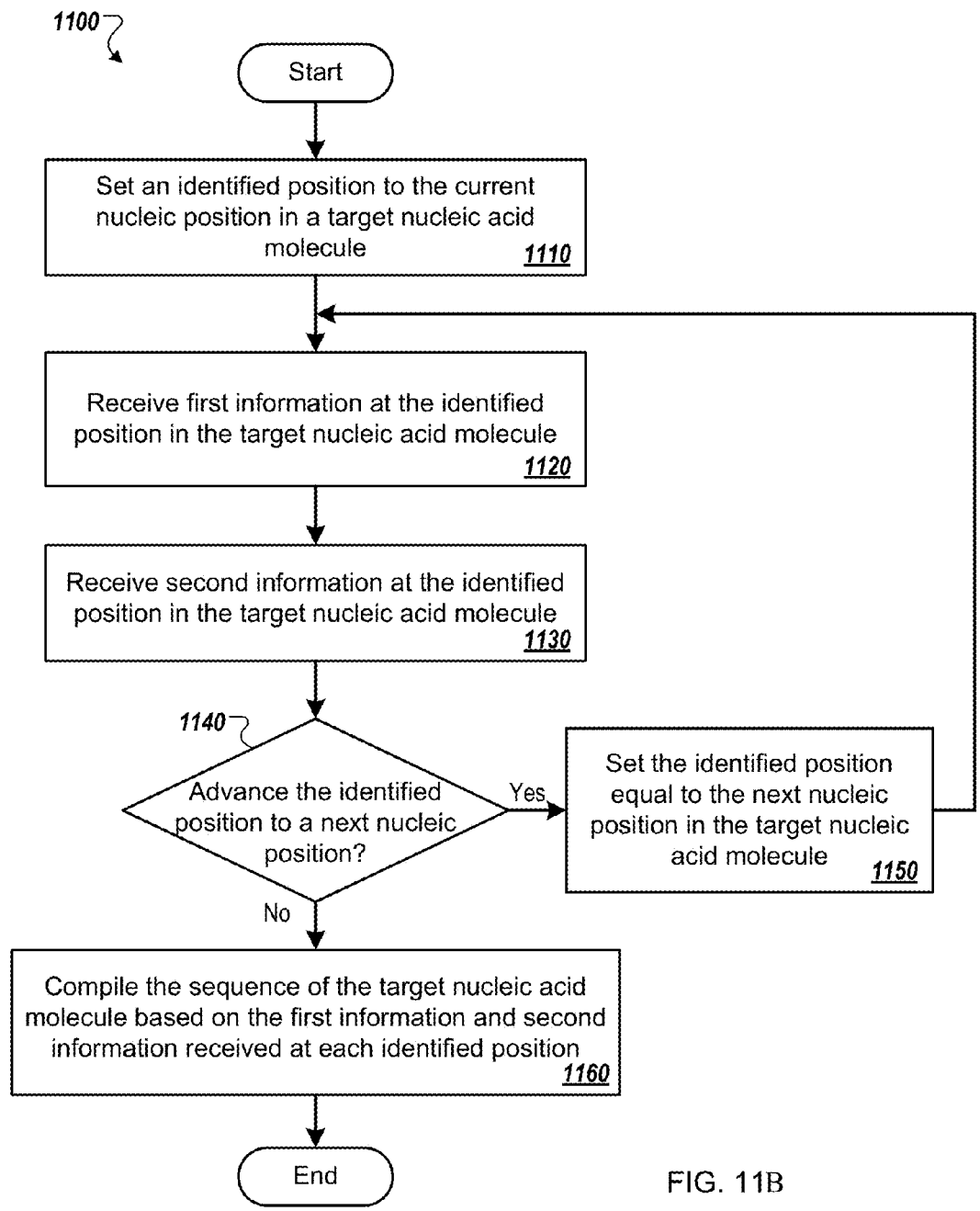
FIG. 11B is a flow diagram illustrating an example process for determining the sequence of a target nucleic acid molecule.

FIG. 11B is a flow diagram illustrating an example process 1100 for determining the sequence of a target nucleic acid molecule. In some examples, the process 1100 can be implemented using one or more computer program applications executed using one or more computing devices. For purposes of illustration, a non-limiting example context is provided that is directed to determining the sequence of a target nucleic acid molecule comprising a rotation tag based upon data obtained during transcription of the target nucleic acid molecule.

The process 1100 starts by setting an identified position to the current nucleic position in a target nucleic acid molecule (1110) being sequenced using the rotation-dependent transcriptional sequencing described herein. An identified position can be, for example, the first nucleotide transcribed, the first nucleotide transcribed from the target nucleic acid molecule (i.e., after the promoter sequences), or any nucleotide position along a target nucleic acid molecule.

First datum (i.e., first information) at the identified position in the target nucleic acid molecule is received (1120) from the rotation-dependent transcriptional sequencing system or provided based upon information from the operation of the rotation-dependent transcriptional sequencing, and second information (i.e., second datum) at the identified position in the target nucleic acid molecule is provided or received (1120). For example, the first datum can be information regarding rotation of the rotation tag. For example, first datum can be a rate of rotation (i.e., degrees of rotation/time), a determination of the presence or absence of rotation, or a change in an established rotational pattern. For example, the second datum can be information regarding the presence and/or availability (e.g., concentration) of one or more nucleoside triphosphates in the sequencing reaction.

The nucleotide at an identified position then can be determined based upon the first and second data. For example, if the first datum indicates a change in the rotational pattern and the second datum indicates the presence of guanine nucleoside triphosphate in the reaction, then the nucleotide at the identified position in the target nucleic acid molecule is determined to be cytosine. Similarly, if the first datum indicates an absence of change in the rotational pattern and the second datum indicates the presence of guanine nucleoside triphosphate in the reaction, the nucleotide at the indicated position in the target nucleic acid molecule is determined to be non-guanine (i.e., adenine, guanine, and thymine).

If it is determined that the identified position can be advanced to a next position (1140), the identified position is set equal to the next nucleic position in the target nucleic acid molecule (1150) and the process 1100 continues (1120). If it is determined that the identified position cannot be advanced to a next position (1140), the sequence of the target nucleic acid molecule based on the first information and second information received at each identified position is compiled (1160) and the process 1100 ends. The identified position cannot be advanced to a next position when transcription can no longer occur due, for example, to completion of transcription of the target nucleic acid molecule or expiration of RNA polymerase activity (e.g., due to decay of enzyme activity).

Embodiments of the subject matter and the operations described in this specification can be implemented in digital electronic circuitry, or in computer software, firmware, or hardware, or in combinations of one or more of them. Embodiments of the subject matter described herein can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, a mobile communication device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described herein can be implemented as operations performed by a data processing apparatus on data stored on one or more computer-readable storage devices or received from other sources. The term "data processing apparatus" encompasses all kinds of apparatus, devices, and machines for processing data including, by way of example, a programmable processor, a mobile communications device, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described herein can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program include, by way of example, both general and special, purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile communications device, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Solid Surface Preparation

An NTA monolayer was prepared as described (see Paik et al., 2005, *Chem. Commun.*, 15:1956-58. Ni-NTA surfaces were obtained by immersing the NTA-functionalized substrates into 10 mM Tris-HCl buffer (pH 8.0) containing 0.1 M $NiCl_2$ for 30 min. The substrates were then rinsed several times with Milli-Q water and dried under a nitrogen stream.

The freshly cleaned substrates were immersed into a distilled toluene solution containing 1% (v/v) 3-glycidyloxypropyl trimethoxysilane under argon for 2 days. After the substrates were removed from the solution, they were rinsed with distilled toluene and dried under a nitrogen stream. The substrates functionalized with epoxy-terminated SAM were incubated in 10 mM Tris-HCl buffer (pH 8.0) containing 2.5 mM N,N bis(carboxymethyl)-L-lysine (NTA) at 60° C. for 4 h. The substrates were rinsed with Milli-Q water and dried in preparation for microcontact printing.

A limited nonspecific binding effect of His-tagged protein to the NTA SAM was observed, demonstrating the NTA SAM to be a suitable surface for fabricating Ni(II) ion patterns with microcontact printing and dip-pen nanolithography techniques.

Example 2

Cloning and Purification of His-Tagged RNA Polymerase

A DNA fragment that encodes the 38 amino acid SBP-tag was synthesized by PCR using pTAGk19 as a template and synthetic DNA oligomers RP46 and RP47 (see below) as primers. The fragment was digested with NcoI and ligated into pBH16117, resulting in pRP6.

SBP-His-RNA polymerase and His-RNA polymerase were expressed and purified as previously described (He et al., 1997, *J. Protein Expression Purif.*, 9:142-51; and Keefe et al, 2001, *J. Protein Expression Purif.*, 23:440-46).

Example 3

Immobilization of RNA Polymerase

The following reaction scheme was followed for the immobilization of RNA polymerase molecules on Si(111): (a) 40% $NH_4F$, 10 min, 25° C.; (b) $Cl_2$ gas, 20 min, 100° C.; (c) mPEG, over-night, vacuum, 150° C.; (d) DSC, DEIDA, DMAP, DMF, overnight, 25° C.; (f) BBTO, diethyl ether, 6 h, 25° C.; (g) $CuSO_4$, ethanol 20 min, 25° C.; (h) 6×His-tagged protein incubation.

Example 4

Microcontact Printing (μCP) and Complex Formation

A 10:1 (v/v) mixture of poly(dimethylsiloxane) (PDMS) and curing agent (Sylgard 184, Dow Corning) was cast against a patterned silicon master to prepare PDMS stamps with 5 micron line features, with a spacing of 3 and 10 micron line features and a spacing of 5 micron. The non-oxidized PDMS stamps were incubated in 10 mM Tris-HCl buffer (pH 8.0) containing 0.1 M NiCl, for about 1 h and then dried with a nitrogen stream. The stamps were brought into contact with a NTA-terminated substrate for 3 min. After peeling off the stamp, the Ni(II)-printed substrates were incubated in about 200 μL of 25 mM Tris-HCl buffer (pH 7.5) containing 100 nM of His-T7 RNAP with ds-DNA, promoter and magnetic tags attached via streptavidin-biotin bonds for 30 min and then rinsed with 10 mM Tris-HCl buffer (pH 8.0) and Milli-Q water to remove excess protein.

Example 5

Tethering and Rotation 2.8 micron SA-conjugated beads (Dynal) and 1.0 micron biotinylated beads were diluted (1:20 and 1:200, respectively) in PBS, and mixed at room temperature for 15 min.

Coverslips were coated with Ni2+-NTA HRP conjugate (Qiagen) and flow chambers were assembled by aligning together slightly separated coverslips as previously described (see, Noji et al., 1997, *Nature*, 386:299-302).

A 4 kb DNA template biotinylated at one end was mixed with SA bead doublets and incubated with 20 nM His-T7 RNAP, 0.3 mM GTP, and 0.1 mM ATP for 2 min to allow the formation of an elongation complex. The sample (~30 µl) was injected into a flow cell, incubated for 5 min, and a magnetic force of 0.1 pN was applied. The flow cells were washed with TB followed by addition of 0.5 mM NTPs.

It was found that positioning the magnet offset from the bead location, i.e. not directly on top but creating an angle with respect to the light source and objective, allows for easier calibration of positional changes and forces.

Example 6

Formation of Rotation-Dependent Transcriptional Sequencing Complex

Figure 2C:
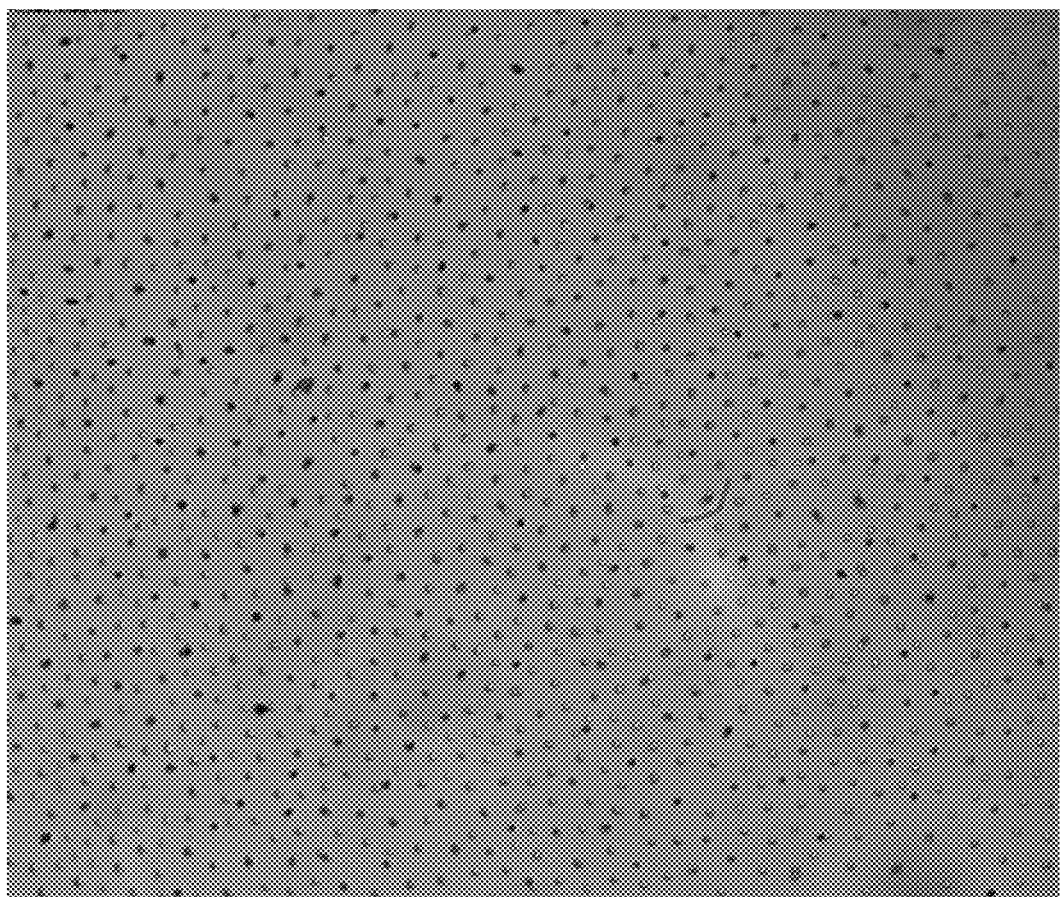
FIG. 2C is a photograph of an array of rotation tags tethered by His-tagged RNA polymerase and a 5.1 Kb DNA template on a passivated solid surface.

FIG. 2C shows an array of rotation tags tethered by a His-tagged RNA polymerase and a 5.1 Kb DNA template on a passivated, nickel-coated glass slide. The "semirandom" array was created via magnetic field application that allows the beads to position themselves in ordered distance with respect to each other. Singlet-, doublet- and triplet-bead-carrying nucleic acids were attached to the surface by flipping the slide upside down so that a conical magnetic field pulled the magnetic tags onto the glass surface in an ordered fashion. Percolation of magnetic beads in two-dimensional space actively created the pattern shown in FIG. 2C. Subsequently, the magnet was removed and the flow chamber was flipped upside down again for the magnet to apply tension to the nucleic acids. The sequencing reaction mix was then delivered to the flow chamber to initiate transcription and sequencing of all molecules in parallel.

Example 7

Template Preparation

DNA template for Sequencing by transcription was prepared by joining together 4.6 kb phage T7 DNA fragment bearing T7 promoter and 0.5 kb biotinylated fragment of Lambda DNA. A 4.6 kb fragment was generated by PCR using #T7pPKI3 forward primer and #T7phi17REV primer containing an XbaI recognition site at the 3' end. A 0.5 kb PCR fragment was generated by PCR using #F3 and #R3 primers in the presence of Biotin-16-dUTP (Roche). After PCR was completed, the purified PCR product was digested with NheI and cleaned up with QIAquick PCR Purification Kit (Qiagen).

After digestion of the PCR product with XbaI, the 4.6 kb piece was joined by overnight ligation at 15° C. with a 0.5 kb biotinylated PCR fragment digested with NheI. The resulting ligation product of 5.1 kb was resolved using 0.7% agarose gel electrophoresis and extracted from the gel using QIAquick Gel Extraction Kit (Qiagen). This DNA was used in the transcription and sequencing experiments.

The following primers were used for PCR: #T7pPKI3: GCA GTAATACGACTCACTATA GGG AGA GGG AGG GAT GGA GCC TTT AAG GAG GTC AAA TGG CTA ACG (SEQ ID NO:1; the T7 promoter sequence is underlined, the bold G is +1 and the bold C is a pause site at position +20); #T7phi17REV: GGC A-T CTA GA-TGC ATC CCT ATG CAG TCC TAA TGC (SEQ ID NO:2; contains Xba site); #F3: GGC AGC TAG CTA AAC ATG GCG CTG TAC GTT TCG C (SEQ ID NO:3; contains NheI restriction site at 5' end); and #R3: AGC CTT TCG GAT CGA ACA CGA TGA (SEQ ID NO:4).

The following table shows the reaction mixture used to prepare a 4.6 Kb fragment from T7 phage containing the T7 promoter. PCR amplification was performed under the following cycling conditions: 94° C. for 30", 32 cycles at 94° C. for 10", 55° C. for 30", 65° C. for 4'10", 65° C. for 10', followed by a 4° C. hold.

| Component | Volume |
| --- | --- |
| 5x LongAmp Buffer with Mg (New England Biolabs) | 60 µl |
| 25 mM NTPs (each) | 3.6 ul |
| 10 mM # T7pPK13 | 12 µl (0.4 mM final) |
| 10 mM #T7phi17REV | 12 µl (0.4 mM final) |
| (50 ng/µl) | 6 µl |
| H₂O | 194.4 µl |
| LongAmp Polymerase (NEB) | 12 µl |
| Total Reaction Volume | 300 µl |

The following table shows the reaction mixture used to prepare a 0.5 Kb lambda fragment containing multiple biotins. PCR amplification was performed under the following cycling conditions: 94° C. for 10', 32 cycles at 94° C. for 10", 55° C. for 30", 72° C. for 1', 72° C. for 7', followed by a hold at 4° C.

| Component | Volume |
| --- | --- |
| 10x TaqGold buffer w/o Mg (Applied Biosystems) | 10 µl |
| 10 µM F3 | 6 µl |
| 10 µM R3 | 6 µl |
| 25 mM MgCl₂ | 10 µl |
| Lambda DNA (50 ng/µl) | 2 µl |
| 1 mM dGTP | 10 µl |
| 1 mM dCTP | 10 µl |
| 1 mM dATP | 10 µl |
| 1 mM dTTP | 6.5 µl |
| 1 mM Bio-16-dUTP | 3.5 µl |
| H₂O | 21 µl |
| TagGold Pol | 5 µl |
| Total Reaction Volume | 100 µl |

Example 8

Single-Molecule Transcription and Sequencing Reaction

Condition 1 (Formation of Bi-Particles Inside the Flow Cell)

1000 µl of 1 micron Dynabeads MyOne Streptavidin T1 were diluted 1:100 in PBS, pulled down by a magnet to wash, the supernatant was removed and the beads were resuspended in 20 µl Buffer B+0.1% BSA. The beads were transferred to a 0.5 ml tube and sonicated for 2 min before infusion into the flow cell.

Non-magnetic polystyrene biotinylated 0.8 micron beads (Kisker, PC-B-0.8) were prepared as follow: 10 µl beads were spun down and resuspended in 10 µl Buffer B+0.1% BSA to produce a stock of washed beads.

A PEG-Cu++ functionalized glass slide (MicroSurfaces, Inc) was passivated with Buffer B+1% BSA.

The following reaction was set up at room temperature and incubated for 3 min at 37° C.

| Component | Volume |
|---|---|
| 10x Buffer A | 0.5 μl |
| Template (5.1 kb PT7pK13-Bio DNA) 6 ng/μl, 1.93 fmoles/μl, or 2 nM (final 0.8 nM) | 2 μl |
| 10x mix of three NTP (0.3 mM ATP + 0.3 mM GTP + 0.1 mM UTP) | 1 μl |
| 4 μM His-T7RNAP (final 0.8 μM; prepared from stock by diluting in Buffer A) | 1 μl |
| H$_2$O | 0.5 μl |
| Total Reaction Volume | 5 μl |

45 μl of Buffer B was added to the reaction mix with T7 RNAP-DNA elongation complexes halted at position +20 of the template, and the mixture was infused into the flow cell over a period of 5 min.

The flow cell was washed with Buffer B, and 1 μM SA magnetic beads (46 μl Buffer B+0.1% BSA mixed with 6 μl washed beads in Buffer B+0.1% BSA) was infused over a period of 12 min. The flow cell was washed with Buffer B+0.1% BSA.

0.8 micron polystyrene biotinylated beads (2 μl of washed beads+48 μl 1×B/0.1% BSA) were infused into the flow cell and incubated for 15 min to form bi-particles with surface tethered magnetic SA beads. The flow cell was washed with Buffer B to remove unbound 0.8 micron polystyrene beads.

Transcription/sequencing was started by infusing Buffer B+250 μM NTPs+10 mM DTT into the flow cell. Four different NTP mixes (each containing less of one of the nucleotides) were used in four different flow cells.

| 1x Buffer A | 1x Buffer B |
|---|---|
| 20 mM Tris pH8.0 | 20 mM Tris pH8.0 |
| 14 mM MgCl2 | 4 mM MgCl2 |
| 10 mM DTT | 0.1 mM DTT |
| 0.1 mM EDTA | 0.1 mM EDTA |
| 20 mM NaCl | 20 mM NaCl |
| 1.5% glycerol | 20 μg/ml BSA |
| 20 μg/ml BSA | |

Condition 2 (Pre-Formed Bi-Particles)

The overall transcription/sequencing reaction was set up as described above in Condition 1, but, instead of sequential deployment of magnetic and polystyrene beads, the bi-particles were pre-formed as follow. 1000 μl of the mix of 1 micron Dynabeads MyOne SA T1 (Dynal) diluted 1:100 in PBS, and 0.8 micron polystyrene biotin beads (Kisker) diluted 1:500, were mixed on a rotator for 30 min at room temperature to form bi-particles. The beads were pulled down with a magnet, the supernatant with un-bound polystyrene particles was removed, and the beads were re-suspended in 20 μl of Buffer B+0.1% BSA. The beads were transferred to a 0.5 ml tube and sonicated for 2 min before adding to the reaction mix.

Example 9

Projected Cost for Whole Genome Sequencing using Rotation-Dependent Transcriptional Sequencing Significantly, one of the advantages of the rotation-dependent transcriptional sequencing described herein is the low cost, particularly considering the very long run capability. The table below shows the projected costs for sequencing the entire human genome.

| Reagent (worth 100 flowchips) | Cost |
|---|---|
| DNA isolation (mini prep kit from Qlagen: can isolate more than 1000 ng) | $ 2.45 |
| DNA fragmentation (Invitrogen Nebulizer, small plastic each only NOT whole machine "Hydroshear") | $ 26.40 |
| DNA end-repair | $ 3.40 |
| T4 DNA ligase | $ 1.50 |
| Buffers | $ 2.00 |
| SA paramagnetic beads 2.8 um (Dynal) | $380.00 |
| Biotinylated 0.9 um beads (Spnerotech) | $ 43.00 |
| 2 oligos for T7 promoter adaptor | $ 0.28 |
| 2 PCR primers | $ 0.01 |
| Biotin-labeling Kit | $ 1.12 |
| Total cost for 100 Flowchips | $460.16 |
| Total flowchips needed to sequence Whole Human genome | 16 |
| Total cost per human genome | $ 73.63 |

It is to be understood that, while the systems, methods and compositions of matter have been described herein in conjunction with a number of different aspects, the foregoing description of the various aspects is intended to illustrate and not limit the scope of the systems, methods and compositions of matter. Other aspects, advantages, and modifications are within the scope of the following claims.

Disclosed are systems, methods and compositions that can be used for, can be used in conjunction with, can be used in preparation for, or are products of the disclosed systems, methods and compositions. These and other materials are disclosed herein, and it is understood that combinations, subsets, interactions, groups, etc. of these systems, methods and compositions are disclosed. That is, while specific reference to each various individual and collective combinations and permutations of these compositions and methods may not be explicitly disclosed, each is specifically contemplated and described herein. For example, if a particular system part, composition of matter or particular method is disclosed and discussed and a number of system parts, compositions or methods are discussed, each and every combination and permutation of the system parts, compositions and methods are specifically contemplated unless specifically indicated to the contrary. Likewise, any subset or combination of these is also specifically contemplated and disclosed.

What is claimed is:

1. A method of determining the sequence of a target nucleic acid molecule having an unknown sequence, comprising:
contacting an RNA polymerase with a target nucleic acid molecule under sequencing conditions, wherein the sequencing conditions comprise the presence of one nucleoside triphosphate or the presence of four nucleoside triphosphates with one of the four nucleoside triphosphates present in a rate-limiting amount, wherein said RNA polymerase is immobilized on a solid substrate, wherein the target nucleic acid molecule comprises a rotation tag that is about 50 nm to about 2 microns in diameter;
detecting the rotational pattern of the rotation tag;
repeating the contacting and detecting steps at least one hundred times; and
determining the sequence of the target nucleic acid molecule based, sequentially, on the presence or absence of a change in the rotational pattern in the presence of the one nucleoside triphosphate or the presence of the four nucleoside triphosphates with the one of the four nucleoside triphosphates present in a rate-limiting amount.

2. The method of claim 1, wherein the RNA polymerase is a bacteriophage RNA polymerase.

3. The method of claim 2, wherein the bacteriophage RNA polymerase is a T7 RNA polymerase.

4. The method of claim 2, wherein the bacteriophage RNA polymerase is a T3 RNA polymerase.

5. The method of claim 1, wherein the RNA polymerase is a bacterial RNA polymerase.

6. The method of claim 5, wherein the bacterial RNA polymerase is an E. coli RNA polymerase.

7. The method of claim 1, wherein the RNA polymerase is immobilized on the solid substrate via a His-tag.

8. The method of claim 1, wherein the target nucleic acid molecule is eukaryotic.

9. The method of claim 1, wherein the target nucleic acid molecule is double-stranded.

10. The method of claim 1, wherein the target nucleic acid molecule is comprised within a biological sample.

11. The method of claim 1, wherein the target nucleic acid molecule comprises a RNA polymerase promoter sequence.

12. The method of claim 1, wherein the rotation tag comprises a first tag and a second tag.

13. The method of claim 12, wherein the first tag is magnetic.

14. The method of claim 1, wherein the solid substrate is glass.

15. The method of claim 1, wherein the sequencing conditions comprise the presence of a single nucleoside triphosphate.

16. The method of claim 1, wherein the sequencing conditions comprise the presence of four nucleoside triphosphates, where a first nucleoside triphosphate of the four nucleoside triphosphates is present in a rate-limiting amount.

17. The method of claim 1, wherein the detecting step comprises projecting light onto the rotation tag.

18. The method of claim 17, wherein the detecting step further comprises observing the rotational pattern via a microscope.

19. The method of claim 1, wherein the detecting step comprises capturing the rotational pattern on a CMOS or CCD.

20. The method of claim 1, wherein the solid substrate is a CMOS or CCD.

21. The method of claim 1, wherein the detecting step comprises capturing the rotational pattern as a magnetic image.

22. The method of claim 21, wherein the magnetic image is captured on a GMR sensor or a MRAM array.

23. The method of claim 1, wherein the detecting step comprises capturing the rotational pattern as an electric field.

24. The method of claim 23, wherein an image is captured on a RAM sensor.

25. The method of claim 1, further comprising applying a directional force on the target nucleic acid molecule.

26. The method of claim 25, wherein the directional force is produced with a magnet.

27. The method of claim 25, wherein the directional force is produced with flow or pressure.

28. A method of determining the sequence of a target nucleic acid molecule having an unknown sequence, comprising:
providing a solid substrate onto which RNA polymerase is immobilized;
contacting the RNA polymerase with the target nucleic acid molecule under first sequencing conditions, wherein the target nucleic acid molecule comprises a rotation tag that is about 50 nm to about 2 microns in diameter, wherein the first sequencing conditions comprise the presence of four nucleoside triphosphates, where a first nucleoside triphosphate of the four nucleoside triphosphates is present in a rate-limiting amount;
detecting the rotational pattern of the rotation tag under the first sequencing conditions;
contacting the RNA polymerase with the target nucleic acid molecule comprising the rotation tag under second sequencing conditions, wherein the second sequencing conditions comprise the presence of four nucleoside triphosphates, where a second nucleoside triphosphate of the four nucleoside triphosphates is present in a rate-limiting amount;

detecting the rotational pattern of the rotation tag under the second sequencing conditions; and contacting the RNA polymerase with the target nucleic acid molecule comprising the rotation tag under third sequencing conditions, wherein the third sequencing conditions comprise the presence of four nucleoside triphosphates, where a third nucleoside triphosphate of the four nucleoside triphosphates is present in a rate-limiting amount;

detecting the rotational pattern of the rotation tag under the third sequencing conditions;

determining positional information of the first, second and third nucleoside triphosphates along the target nucleic acid molecule based on the changes in the rotational pattern under the first, second and third sequencing conditions; and repeating the contacting and detecting steps under first sequencing conditions, second sequencing conditions and third sequencing conditions at least one hundred times.

29. The method of claim 28, wherein the RNA polymerase is a bacteriophage RNA polymerase.

30. The method of claim 29, wherein the bacteriophage RNA polymerase is a T7 RNA polymerase.

31. The method of claim 29, wherein the bacteriophage RNA polymerase is a T3 RNA polymerase.

32. The method of claim 28, wherein the RNA polymerase is a bacterial RNA polymerase.

33. The method of claim 32, wherein the bacterial RNA polymerase is an *E. coli* RNA polymerase.

34. The method of claim 28, wherein the RNA polymerase is immobilized on the solid substrate via a His-tag.

35. The method of claim 28, wherein the target nucleic acid molecule is eukaryotic.

36. The method of claim 28, wherein the target nucleic acid molecule is double-stranded.

37. The method of claim 28, wherein the target nucleic acid molecule is comprised within a biological sample.

38. The method of claim 28, wherein the target nucleic acid molecule comprises a RNA polymerase promoter sequence.

39. The method of claim 28, wherein the rotation tag comprises a first tag and a second tag.

40. The method of claim 39, wherein the first tag is magnetic.

41. The method of claim 28, wherein the solid substrate is glass.

42. The method of claim 28, wherein the detecting step comprises projecting light onto the rotation tag.

43. The method of claim 42, wherein the detecting step further comprises observing the rotational pattern via a microscope.

44. The method of claim 28, wherein the detecting step comprises capturing the rotational pattern on a CMOS or CCD.

45. The method of claim 28, wherein the solid substrate is a CMOS or CCD.

46. The method of claim 28, wherein the detecting step comprises capturing the rotational pattern as a magnetic image.

47. The method of claim 46, wherein the magnetic image is captured on a GMR sensor or a MRAM array.

48. The method of claim 28, wherein the detecting step comprises capturing the rotational pattern as an electric field.

49. The method of claim 48, wherein an image is captured on a RAM sensor.

50. The method of claim 28, further comprising applying a directional force on the target nucleic acid molecule.

51. The method of claim 50, wherein the directional force is produced with a magnet.

52. The method of claim 50, wherein the directional force is produced with flow or pressure.

53. A method of determining the sequence of a target nucleic acid molecule having an unknown sequence, comprising:

contacting an RNA polymerase with a target nucleic acid molecule under sequencing conditions, wherein the sequencing conditions comprise the presence of one nucleoside triphosphate or the presence of four nucleoside triphosphates with one of the four nucleoside triphosphates present in a rate-limiting amount, wherein said RNA polymerase is immobilized on a solid substrate, wherein the target nucleic acid molecule comprises a rotation tag that is about 50 nm to about 2 microns in diameter;

detecting the rotational pattern of the rotation tag;

repeating the contacting and detecting steps at least twenty times; and determining the sequence of the target nucleic acid molecule based, sequentially, on the presence or absence of a change in the rotational pattern in the presence of the one nucleoside triphosphate or the presence of the four nucleoside triphosphates with the one of the four nucleoside triphosphates present in a rate-limiting amount.

54. The method of claim 53, wherein the contacting and detecting steps are repeated at least thirty times.

55. The method of claim 53, wherein the contacting and detecting steps are repeated at least forty times.

56. The method of claim 53, wherein the contacting and detecting steps are repeated at least fifty times.

57. The method of claim 1, wherein the contacting and detecting steps are repeated at least 500 times.

58. The method of claim 1, wherein the contacting and detecting steps are repeated at least 1000 times.

59. The method of claim 28, wherein the contacting and detecting steps under first sequencing conditions, second sequencing conditions and third sequencing conditions are repeated at least 500 times.

60. The method of claim 28, wherein the contacting and detecting steps under first sequencing conditions, second sequencing conditions and third sequencing conditions are repeated at least 1000 times.

* * * * *